(12) United States Patent
DeLuca et al.

(10) Patent No.: US 8,455,467 B2
(45) Date of Patent: Jun. 4, 2013

(54) 2-METHYLENE-VITAMIN D ANALOGS AND THEIR USES

(71) Applicant: Wisconsin Alumni Research Foundation, Madison, WI (US)

(72) Inventors: Hector F. DeLuca, Deerfield, WI (US); Lori A. Plum, Arena, WI (US); Rafal Sicinski, Warsaw (PL); Izabela Sibilska, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/647,641

(22) Filed: Oct. 9, 2012

(65) Prior Publication Data

US 2013/0102573 A1      Apr. 25, 2013

Related U.S. Application Data

(60) Provisional application No. 61/550,147, filed on Oct. 21, 2011.

(51) Int. Cl.
*A61K 31/59* (2006.01)
*C07C 401/00* (2006.01)

(52) U.S. Cl.
USPC .......................................... 514/167; 552/653

(58) Field of Classification Search
USPC .......................................... 514/167; 552/653
See application file for complete search history.

(56) References Cited

U.S. PATENT DOCUMENTS

| | | | |
|---|---|---|---|
| 4,666,634 A | 5/1987 | Miyamoto | |
| 5,086,191 A | 2/1992 | DeLuca et al. | |
| 5,536,713 A | 7/1996 | DeLuca et al. | |
| 5,843,928 A | 12/1998 | DeLuca et al. | |
| 5,936,133 A | 8/1999 | DeLuca et al. | |
| 5,945,410 A | 8/1999 | DeLuca et al. | |
| 6,392,071 B1 | 5/2002 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 2011/0082121 A1 | 4/2011 | Deluca et al. | |

FOREIGN PATENT DOCUMENTS

WO           9841501 A1      9/1998

OTHER PUBLICATIONS

Sibilska et al., abstract of e-publication on Mar. 27, 2010 (Journal of Steroid Biochemistry and Molecular Biology, vol. 121(1-2) (Jul. 2010) 51-55).*

Osterm et al., "24- and 26-homo-1,25-dihydroxyvitamin D3: Preferential Activity in Inducing Differentiation of Human Leukemia Cells HL-60 in vitro", Proc. Natl. Acad. Sci. USA, 1987, 84: 2610-2614.

(Continued)

*Primary Examiner* — Sabiha N Qazi
(74) *Attorney, Agent, or Firm* — Andrus, Sceales, Starke & Sawall, LLP

(57) ABSTRACT

This invention discloses 2-methylene-vitamin D analogs, and specifically (20S)-25-hydroxy-2-methylene-vitamin $D_3$ and (20R)-25-hydroxy-2-methylene-vitamin $D_3$, as well as pharmaceutical uses therefor. These compounds exhibit relatively high binding activity and pronounced activity in arresting the proliferation of undifferentiated cells and inducing their differentiation to the monocyte thus evidencing use as an anticancer agent especially for the treatment or prevention of osteosarcoma, leukemia, colon cancer, breast cancer, skin cancer or prostate cancer. These compounds also have relatively high calcemic activities evidencing use in the treatment of bone diseases.

48 Claims, 8 Drawing Sheets

OTHER PUBLICATIONS

Perlman et al., "1alpha,25-dihyroxyvitamin D3, A Novel Vitamin D-related Compound with Potential Therapeutic Activity", Tetrahedron Letters, 1990, 31: 1823-1824.

Okano et al., "Regulatory Activites of 2beta-(3-Hydroxypropoxy)-1alpha,25-Dihydroxyvitamin D3, A Novel Synthetic Vitamin D3 Derivative, on Calcium Metabolism", Biochem. Biophys. Res. Commun., 1989, 163(3): 1444-1449.

Miyamoto et al., "Synthetic Studies of Vitamin D Analogs. XIV. Synthesis and Calcium Regulating Activity of Vitamin D3 Analogs Bearing a Hydroxyalkoxy Group at the 2beta-Position", Chem. Pharm. Bull., 1993, 41(6): 1111-1113.

Nishii et al., "The Development of Vitamin D3 Analogs for the Treatment of Osteoporosis", Osteoporosis International, 1993, 1: 190-193.

Inhoffen et al., "Studies in the Vitamin D Series,XXI: Hydrine Compounds from Bitamin D3", Chemische Berichte, 1957, 90: 664-673.

Sicinski et al., "New 1alpha,25-Dihydroxy-19-norvitamin D3 Compounds of High Biological Activity: Synthesis and Biological Evaluation of 2-Hydroxymethyl, 2-Methyl, and 2-Methylene Analogs", J. Med. Chem., 1998, 41: 4662-4674.

Sicinski et al., "New Highly Calcemic 1alpha,25-dihydroxy-19-Norvitamin D3 Compounds with Modified Side Chain: 26,27-dihomo- and 26,27-dimethylene Analogs in 20S-Series", Steroids, 2002, 67: 247-256.

Grzywacz et al., "2-Methylene Analogs of 1alpha-hydroxy-19-norvitamin D3; Synthesis, Biological Activities of Docking to the Ligand Binding Domain of the Rat Vitamin D Receptor", J. Steroid Biochem, 2004, 89-90: 13-17.

Windaus et al., "The Constitution of Vitamin D2: Part II", Annalen der Chemie, 1936, 524: 295-299.

Posner et al., "Stereocontrolled Total Synthesis of Calcitrol Derivatives: 1,25-Dihyroxy-2-(4'-hydroxybutyl)vitamin D3 Analogs of an Osteoporosis Drug", Journal of Organic Chemistry, 1994, 59: 7855-7861.

Posner et al., "2-Fluoroalkyl A-Ring Analogs of 1,25-Dihyroxyvitamin D3. Stereocontrolled Total Synthesis via Intramolecular and Intermolecular Diels-Alder Cycloadditions. Preliminary Biological Testing", Journal of Organic Chemistry, 1995, 60: 4617-4626.

Perlman et al., "Novel Synthesis of 19-Nor-Vitamin D Compounds", Tetrahedron Letters, 1991, 32: 7663-7666.

Baggiolini et al., "Stereocontrolled Total Synthesis of 1[alpha],25-Dihydroxycholecaliferol and 1[alpha],25-Dihydroxyergocalciferol", Journal of Organic Chemistry, 1986, 51: 3098-3108.

Arbour et al., "A Highly Sensitive Method for Large-Scale Measurements of 1,25-Dihydroxyvitamin D", Analytical Biochemistry, 1998, 255: 148-154.

Collins et al., "Normal Functional Characteristics of Cultured Human Promyelocytioc Leukemia Cells (HL-60) After Induction of Differentiation by Dimethylsulfoxide", The Journal of Experimental Medicine, 1979, 149: 969-974.

Sibilska et al., "1-Desoxy Analog of of 2MD: Synthesis and Biological Activity of (20S)-25-Hydroxy-2-Mehtylene-19-Norvitamin D3", J. of Steroid Biochemistry and Molecular Biology, 2010, 121: 51-55.

Peleg et al., "Low-Calcemic, Highly Antiproliferative, 1-Difluoromethyl Hybrid Analogs of the Natural Hormone 1 [alpha],25-Dihydroxyvitamin D3: Design, Synthesis, and Preliminary Biological Evaluation", Journal of Medicinal Chemistry, 2006, 49(25): 7513-7517.

International Search Report and Written Opinion, PCT International Application No. PCT/US2012/059315, mailed Dec. 7, 2012.

Arndt, "Diazomethane", Organic Synthesis, Coll., 1935, 15: 3.

Arndt, "Nitrosomethylurea", Organic Synthesis, Coll., 1935, 15: 48.

Barrack et al., "Potential Inhibitors of Vitamin D Metabolism: An Oxa Analogue of Vitamin D", Journal of Organic Chemistry, 1988, 53: 1790-1796.

Desmaele et al., "A New Synthesis of a New Cycle of 1S-Hydroxycholecalciferol", Tetrahedron Letters, 1985 26(40): 1941-4944.

Hayashi, et al., "Direct Proline-Catalyzed Asymmetric Alpha-Aminoxylation of Aldehydes and Ketones", Journal of Organic Chemistry, 2004, 69: 15966-5973.

Mascarenas et al., "Palladium-Catalysed Coupling of Vinyl Triflates with Enynes and its Application to the Synthesis of 1Alpha,25-Dihydroxyvitamin D3", Tetrahedron, 1991, 47(20:21): 3485-3498.

Reetz, "Alpha-Methylation of Ketones via Manganese-Enolates: Absence of Undesired Polyalkylation", Tetrahedron Letters, 1993, 34(46): 7395-7398.

Sanches-Abella et al., "Synthesis and Biological Activity of Previtamin D3 Analogues with A-ring Modifications", Bioorganic & Medicinal Chemistry, 2008, 16: 10244-10250.

* cited by examiner

2-METHYLENE-VITAMIN D ANALOGS AND THEIR USES

BACKGROUND OF THE INVENTION

This invention relates to vitamin D compounds, and more particularly to 2-Methylene-Vitamin D analogs and their pharmaceutical uses, and especially (20S)-25-hydroxy-2-methylene-vitamin $D_3$, its biological activities, and its pharmaceutical uses, as well as (20R)-25-hydroxy-2-methylene-vitamin $D_3$, its biological activities, and its pharmaceutical uses. This latter compound can also be named simply as 2-methylene-25-hydroxy-vitamin $D_3$ since the 20-methyl substituent is in its natural or "R" orientation.

The natural hormone, $1\alpha,25$-dihydroxyvitamin $D_3$ and its analog in the ergosterol series, i.e. $1\alpha,25$-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of $1\alpha,25$-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of $1\alpha,25$-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of $1\alpha,25$-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. $1\alpha$-hydroxy-2-methylene-19-nor-pregnacalciferol is described in U.S. Pat. No. 6,566,352 while $1\alpha$-hydroxy-2-methylene-19-nor-homopregnacalciferol is described in U.S. Pat. No. 6,579,861 and $1\alpha$-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to $1\alpha,25$-dihydroxyvitamin $D_3$. Their biological activities make these compounds excellent candidates for a variety of pharmaceutical uses, as set forth in the '352, '861 and '622 patents.

Analogs of the natural hormone $1\alpha,25$-dihydroxyvitamin $D_3$ characterized by the transposition of the A-ring exocyclic methylene group from carbon 10 (C-10) to carbon 2 (C-2) (e.g., $1\alpha,25$-dihydroxy-2-methylene-19-nor-vitamin D analogs) have been synthesized and tested [see Sicinski et al., J. Med. Chem., 41, 4662 (1998); Sicinski et al., Steroids 67, 247 (2002); and, DeLuca et al., U.S. Pat. Nos. 5,843,928; 5,936,133 and 6,382,071)]. Molecular mechanics studies performed on these analogs predict that a change of A-ring conformation may cause flattening of the cyclohexanediol ring. Molecular mechanics calculations and NMR studies also predict that the A-ring conformational equilibrium would be ca. 6:4 in favor of the conformer having an equatorial $1\alpha$-OH. It was further predicted that introduction of the 2-methylene group into 19-nor-vitamin D carbon skeleton would change the character of its $1\alpha$- and $3\beta$-A-ring hydroxyls. They would both be in allylic positions similar to the $1\alpha$-hydroxyl group in the molecule of the natural hormone [i.e., $1\alpha,25$-$(OH)_2D_3$]. It was found that $1\alpha,25$-dihydroxy-2-methylene-19-nor-vitamin D analogs are characterized by significant biological potency. In addition, the biological potency of such analogs may be enhanced dramatically where "unnatural" (20S)-configuration is present. Taking into account these findings, the present invention is aimed at vitamin D compounds characterized by the presence of an A-ring exocyclic methylene group at carbon 2 (C-2) (e.g., 2-methylene-vitamin D analogs). Although these analogs lack $1\alpha$-OH, that is important for biological activity, such hydroxyl group can be potentially introduced enzymatically in the living organisms.

SUMMARY OF THE INVENTION

The present invention is aimed at vitamin D compounds characterized by not only having the A-ring exocyclic methylene group at carbon 10 (C-10), but also by the presence of an additional exomethylene substituent at carbon 2 (C-2) (i.e., 2-methylene-vitamin D analogs). These analogs also lack a $1\alpha$-OH group, and thus the present invention is directed toward 2-methylene-vitamin D analogs, and their pharmaceutical uses, and more specifically toward (20S)-25-hydroxy-2-methylene-vitamin $D_3$, its biological activity, and various pharmaceutical uses for this compound, as well as (20R)-25-hydroxy-2-methylene-vitamin $D_3$, its biological activities, and its pharmaceutical uses.

Structurally these 1-desoxy-2-methylene-vitamin D analogs are characterized by the general formula I shown below:

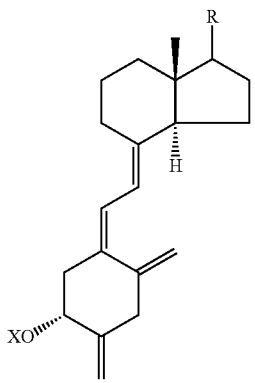

I where X is selected from the group consisting of hydrogen and a hydroxy-protecting group, and where the group R represents any of the typical side chains known for vitamin D type compounds. Thus, R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

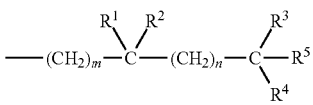

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

Specific important examples of side chains are the structures represented by formulas (a), (b), (c), (d) and (e) below with natural 20R-configuration, i.e., the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e).

Additional important examples of side chains are the structures represented by formulas (a), (b), (c), (d) and (e) below having the 20-epi or 20S-configuration, i.e., the side chain as it occurs in (20S)-25-hydroxyvitamin D$_3$ (a); (20S)-vitamin D$_3$ (b); (20S)-25-hydroxyvitamin D$_2$ (c); (20S)-vitamin D$_2$ (d); and the C-24 epimer of (20S)-25-hydroxyvitamin D$_2$ (e).

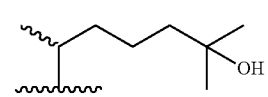

(a)

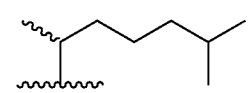

(b)

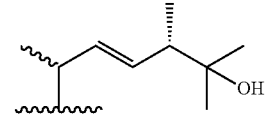

(c)

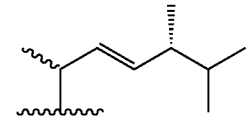

(d)

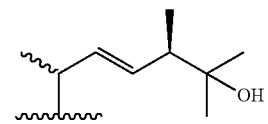

(e)

The wavy line to the carbon 20 indicates that carbon 20 may have either the R or S configuration.

The preferred analogs are (20S)-25-hydroxy-2-methylene-vitamin D$_3$ (which is referred to herein as "1D-QMS") which has the following formula Ia:

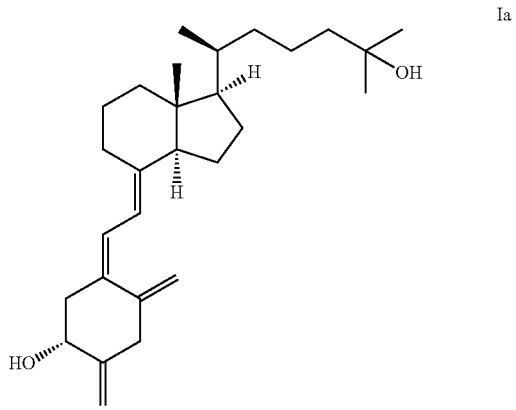

Ia and (20R)-25-hydroxy-2-methylene-vitamin D$_3$ (which is referred to herein as "1D-QM") which has the following formula Ib:

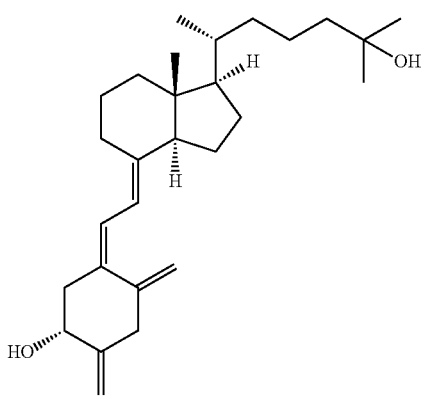

Compound Ia may also be named "(20S)-2-methylene-25-hydroxy-vitamin $D_3$," and Compound Ib may also be named "2-methylene-25-hydroxy-vitamin $D_3$" herein.

The above compounds of formula I, especially formula Ia and Ib, exhibit a desired, and highly advantageous, pattern of biological activity. These compounds are characterized by relatively high binding to vitamin D receptors, i.e. they bind with about the same affinity as 1α,25-dihydroxyvitamin $D_3$. They are only slightly less potent causing differentiation of HL-60 cells than 1,25(OH)$_2$D$_3$. They also exhibit relatively high activity in their ability to mobilize calcium from bone, and in their ability to promote intestinal calcium transport, as compared to 1α,25-dihydroxyvitamin $D_3$.

In vivo, distinct activity profiles emerge most likely due to the ability of these compounds to act as prodrugs since 1-hydroxylation can occur in a regulated manner and the half-life of the compound is predicted to be extended. These analogs may serve as important therapies for diseases where less frequent dose administration is desirable, such as bone diseases like senile osteoporosis, postmenopausal osteoporosis, steroid-induced osteoporosis, low bone turnover osteoporosis, osteomalacia, and renal osteodystrophy.

The above compounds I, and particularly Ia and Ib, have relatively high binding affinity, are characterized by relatively high cell differentiation activity, and have relatively high calcemic activities. Thus, these compounds have potential as anti-cancer agents and provide therapeutic agents for the prevention or treatment of osteosarcoma, leukemia, colon cancer, breast cancer, skin cancer and prostate cancer.

One or more of the compounds may be present in a composition to treat or prevent the above-noted diseases in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually, or parenterally in dosages of from about 0.01 μg/day to about 1000 μg/day, preferably from about 0.1 μg/day to about 500 μg/day.

BRIEF DESCRIPTION OF THE DRAWINGS

FIG. 1 is a graph illustrating the relative activity of 1D-QMS and 1,25(OH)$_2$D$_3$ to compete for binding with [$^3$H]-1,25-(OH)$_2$-D$_3$ to the full-length recombinant rat vitamin D receptor;

FIG. 2 is a graph illustrating the percent HL-60 cell differentiation as a function of the concentration of 1D-QMS and 1,25(OH)$_2$D$_3$;

FIG. 3 is a bar graph illustrating the bone calcium mobilization activity of 1,25(OH)$_2$D$_3$ as compared to 1D-QMS; and FIG. 4 is a bar graph illustrating the intestinal calcium transport activity of 1,25(OH)$_2$D$_3$ as compared to 1D-QMS.

FIG. 5 is a graph illustrating the relative activity of 1D-QM and 1,25(OH)$_2$D$_3$ to compete for binding with [$^3$H]-1,25-(OH)$_2$-D$_3$ to the full-length recombinant rat vitamin D receptor;

FIG. 6 is a graph illustrating the percent HL-60 cell differentiation as a function of the concentration of 1D-QM and 1,25(OH)$_2$D$_3$;

FIG. 7 is a bar graph illustrating the bone calcium mobilization activity of 1,25(OH)$_2$D$_3$ as compared to 1D-QM; and FIG. 8 is a bar graph illustrating the intestinal calcium transport activity of 1,25(OH)$_2$D$_3$ as compared to 1D-QM.

DETAILED DESCRIPTION OF THE INVENTION

Figure 1:
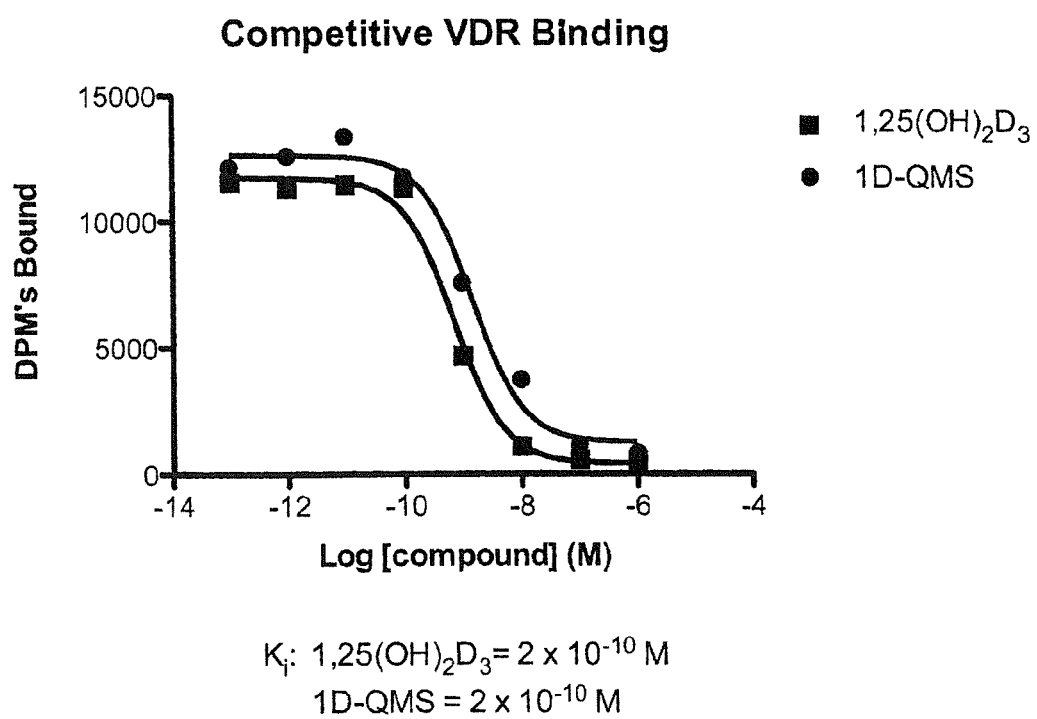
FIGS. 1-4 illustrate various biological activities of (20S)-25-hydroxy-2-methylene-vitamin. $D_3$, hereinafter referred to as "1D-QMS," as compared to the native hormone 1α,25-dihydroxyvitamin $D_3$, hereinafter "1,25(OH)$_2$D$_3$."

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

The preparation of 2-methylene-vitamin D analogs of the basic structure I can be accomplished by a common general method, i.e., a Sonogashira coupling of a bicyclic vinyl compound II with the dienyne III:

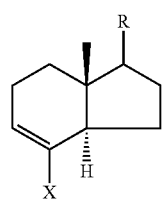
II

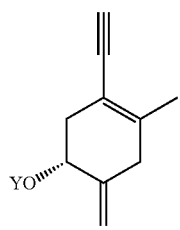
III

In the structures II and III, group X represents a leaving group selected from halogen (iodine, bromine or chlorine) and alkyl- or aryl-sulphonyloxy such as mesyloxy, tosyloxy or—most preferably—trifloxy. Groups Y and R represent groups defined above; Y being preferably hydroxy-protecting group, it being also understood that any functionalities in R that might be sensitive, or that interfere with the coupling reaction, be suitable protected as is well-known in the art. The process shown above represents an application of the convergent synthesis concept, which has been applied effectively for the preparation of vitamin D compounds [Mascarenas et al., Tetrahedron 47, 3485 (1991), Barrack et al., J. Org. Chem., 53, 1790 (1988); Sanchez-Abella et al., Bioorg. Med. Chem. 16, 10244 (2008)].

Bicyclic compounds of the general structure II are known, or can be easily prepared by known methods from the corresponding Windaus-Grundmann type ketones. Specific important examples of such known bicyclic ketones are the structures with the side chains (h), (i), (j), (k), (l), (m), and (n) below described above, i.e., 25-hydroxy Grundmann's ketone (h) [Baggiolini et al., J. Org. Chem., 51, 3098 (1986)]; Grundmann's ketone (i) [Inhoffen et al., Chem. Ber., 90, 664 (1957)]; 25-hydroxy Windaus ketone (j) [Baggiolini et al., J. Org. Chem., 51, 3098 (1986)]; Windaus ketone (k) [Windaus et al., Ann., 524, 297 (1936)]; (20S)-25-hydroxy Grundmann's ketone (l) [Sicinski et al., J. Med. Chem., 41, 4662 (1998)]; (20S)-Grundmann's ketone (m) [Grzywacz et al., J. Steroid Biochem. Mol. Biol., 89-90, 13 (2004)]; and (20S)-25-methyl Grundmann's ketone (n) [Grzywacz et al., J. Steroid Biochem. Mol. Biol., 89-90, 13 (2004)]:

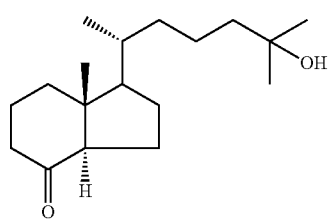
(h)

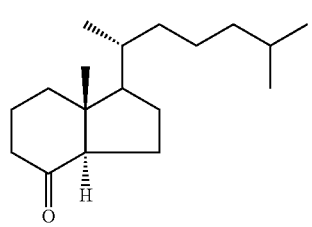
(i)

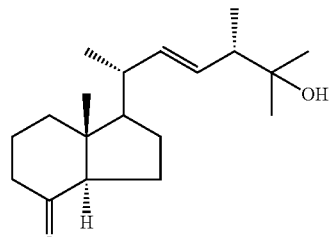
(j)

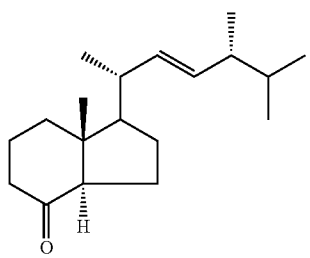
(k)

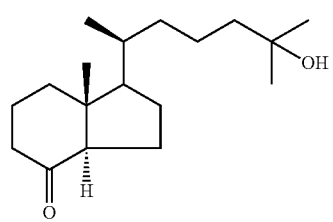
(l)

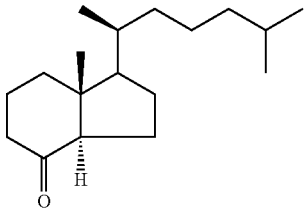
(m)

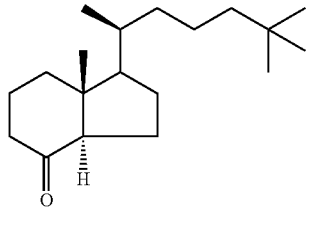
(n)

Regarding the preparation of the dienynes of the structure III, alternative synthetic routes were established. As set forth in SCHEME I, an achiral, commercially available acetal-ketone 1, was α-methylated using the method of Reetz et al. [Tetr. Lett., 34, 7395 (1993)]. Then, the keto group in the formed 2 was reduced and the obtained alcohol 3 (a diastereomeric mixture) was subsequently esterified with pivaloyl chloride. Only the prevailing trans-isomer underwent this reaction and, therefore, the resulted ester 4 was a mixture of (S,S) and (R,R)-enantiomers. The carbonyl group in 4 was deprotected in the reaction with the Lewis acid (FeCl$_3$) and the formed cyclohexanone 5 was enantioselectively α-hydroxylated using the method elaborated by Hayashi et al. [J. Org. Chem., 69, 5966 (2004)] and involving the reaction of a ketone with nitrosobenzene in the presence of a catalytic amount of L-proline. Three main products 6a,b,c were isolated in comparable quantities. The introduced secondary hydroxyl in the product 6a was silylated and the protected compound 7 was subjected to the Wittig reaction with an ylide generated from methyltriphenylphosphonium bromide and n-butyllithium. The pivaloyl protecting group in the formed olefin 8 was removed by treatment with DIBAL and the obtained cyclohexanol derivative 9 was oxidized to the ketone 10. Its reaction with lithium acetylide provided tertiary alcohol 11 which was dehydrated in two-step process (mesylation and reduction of the mesylate). After removal of the TMS group from the ethynyl substituent in the obtained product 12, the desired A-ring fragment 13 was prepared.

SCHEME II shows the subsequent Sonogashira coupling of the obtained A-ring dienyne 13 with an enol triflate 14 [Sanchez-Abella et al., Bioorg. Med. Chem. 16, 10244 (2008)], representing C,D-fragment derived from the protected 25-hydroxy Grundmann's ketone. The reaction should be preferentially carried out in the presence of bis(triphenylphosphine)palladium (II) acetate-copper (I) iodide catalyst and diethylamine. The coupling resulted in formation of the trienyne 15 which was further hydrogenated in the presence of Lindlar catalyst and quinoline. The expected product of such catalytic hydrogenation, previtamin D compound 16, was purified by preparative TLC and subjected to the thermal reaction in hexane. The protected vitamin D compound 17 was isolated by HPLC, and after hydroxyls deprotection with tetrabutylammonium fluoride provided the desired 25-hydroxy-2-methylene-vitamin D$_3$ (18). This synthetic path is described in EXAMPLE I herein.

SCHEME III and SCHEME IV show a different synthetic sequence leading to the building block 26 and to the final vitamin 32. As set forth in SCHEME III, the hydroxy ester 20, easily prepared from the commercially available (−)-quinic acid (19) by the method elaborated by Sibilska et al. [J. Steroid Biochem. Mol. Biol., 121, 51 (2010)], was used as a starting compound and the synthetic strategy was based on the work of Desmaele and Tanier [Tetrahedron Lett., 26, 4941 (1985)]. Thus, the tertiary alcohol was dehydrated and the formed α,β-unsaturated ester 21 subjected to reaction with diazomethane. Such stereospecific 1,3-dipolar cycloaddition provided the expected bicyclic product 22. The subsequent thermolysis of the adduct 22 lead to efficient extrusion of nitrogen and formation of unsaturated ester 23. Its reduction with DIBALH furnished the allylic alcohol 24 that was oxidized with PDC to the α,β-unsaturated aldehyde 25. On treatment of this product with (trimethylsilyl)diazomethane the desired A-ring fragment 26 was prepared.

SCHEME IV shows a preparation of the enol triflate 28, representing a C,D-fragment, from the protected (20S)-25-hydroxy Grundmann's ketone 27 [Sicinski et al., J. Med. Chem., 41, 4662 (1998)]. Treatment of the enol form of 27, generated by addition of the LDA at −78° C., with N-phenyltriflimide afforded 28. The subsequent Sonogashira coupling of the obtained A-ring dienyne 26 with an enol triflate 28 resulted in formation of the trienyne 29 which was further hydrogenated in the presence of Lindlar catalyst and quinoline. The expected product of such catalytic hydrogenation, previtamin D compound 30, was purified by preparative TLC and subjected to the thermal reaction in hexane. The protected vitamin D compound 31 was isolated by HPLC, and after hydroxyls deprotection with tetrabutylammonium fluoride provided the desired (20S)-25-hydroxy-2-methylene-vitamin D$_3$ (32). This synthetic path is described in EXAMPLE II herein.

As it is evident from EXAMPLE I and EXAMPLE II, other vitamin D analogs having the different side-chains may be synthesized by the methods set forth herein.

This invention is described by the following illustrative examples. In these examples specific products identified by Arabic numerals (e.g., 1, 2, 3, etc) refer to the specific structures so identified in the preceding description and in the SCHEME I, SCHEME II, SCHEME III and SCHEME IV.

EXAMPLES

Chemistry. Melting points (uncorrected) were determined on a Thomas-Hoover capillary melting-point apparatus. Optical rotations were measured in chloroform using a Perkin-Elmer 241 automatic polarimeter at 22° C. Ultraviolet (UV) absorption spectra were recorded with a Perkin-Elmer Lambda 3B UV-VIS spectrophotometer in ethanol. $^1$H nuclear magnetic resonance (NMR) spectra were recorded in deuteriochloroform at 200, 400 and 500 MHz with a Varian Unity, Bruker DMX-400 and Bruker DMX-500 spectrometers, respectively. $^{13}$C nuclear magnetic resonance (NMR) spectra were recorded in deuteriochloroform at 50, 100 and 125 MHz with a Varian Unity, Bruker DMX-400 and Bruker DMX-500 spectrometers, respectively. Chemical shifts (δ) were reported downfield from internal Me$_4$Si (δ0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

In the description of the proton MMR signals of compounds 6a-6c orientation of the hydroxyl group introduced in the proline catalyzed process was arbitrarily established as "a"; the same assignment was used for their derivatives 7-13. In the description of the proton MMR signals of compounds 20-26 orientation of the OTBS group was arbitrarily established as "a".

Example I

Preparation of 25-hydroxy-2-methylene-vitamin D$_3$ (18)

(a) α-Methylation of a ketone 1 (SCHEME I). 7-Methyl-1,4-dioxa-spiro[4.5]decan-8-one (2). A solution of 1,4-cyclohexanedione monoethylene ketal (1, 5.12 g, 32.96 mmol) in dry THF (20 mL) was added to a solution of LiHMDS (1.0 M in THF, 33.0 mL, 33.0 mmol) under argon at −78° C. and the mixture was stirred for 40 min. After warming up to room temperature DMPU (13.3 mL) was added. Stirring was continued for additional 10 min, and the enolate solution was cannulated to the flask containing anhydrous MnBr$_2$ (7.83 g, 36.46 mmol) and the mixture was stirred until clear reddish-brown solution was obtained (approximately 30 min). The methyl iodide (2.5 mL, 40.0 mmol) was then added, and after 4 h the reaction was quenched by the addition of saturated NH$_4$Cl and EDTA. Materials were extracted with diethyl ether, dried over MgSO$_4$, and concentrated. Purification by column chromatography on silica (3→5% ethyl acetate/hexane gradient) gave an oily α-methyl ketone 2 (3.72 g, 67%).

2: $^1$H NMR (200 MHz, CDCl$_3$) δ 1.02 (3H, d, J=6.6 Hz, CH$_3$), 1.72 (1H, br t, J=13.2 Hz), 2.04 (3H, br m), 2.35 (1H, ddd, J=14.4, 4.9, 2.9 Hz), 2.69 (2H, m), 4.02 (4H, m, O—CH$_2$CH$_2$—O); $^{13}$C NMR (50 MHz, CDCl$_3$) δ 14.48, 34.82, 38.17, 41.44, 42.92, 64.78, 64.90, 107.55, 212.08; HRMS (ESI) exact mass calcd for C$_9$H$_{14}$O$_3$Na (M$^+$+Na) 193.0841, measured 193.0836.

(b) Reduction of the ketone 2. Cis- and trans-7-methyl-1,4-dioxa-spiro[4.5]decan-8-ols (3). To a solution of ketone (2, 2.99 g, 17.57 mmol) in anhydrous MeOH (83 mL) was slowly added NaBH$_4$ (1.039 g, 27.45 mmol) at 0° C. After 10 min cooling bath was removed, and stirring was continued at room temperature for 1 h. Brine was added and mixture was extracted with ethyl acetate, washed with 2N NaOH solution, dried over MgSO$_4$, and concentrated. The resulted crude mixture of the alcohols 3 (2.87 g, 95%; cis:trans isomer ratio of 1:13.3) was sufficiently pure to be used in the second synthetic step. Separation of the isomers could be achieved by column chromatography on silica using hexane/ethyl acetate (9:1) solvent system.

3 (cis-isomer): $^1$H NMR (200 MHz, CDCl$_3$) δ 0.98 (3H, d, J=6.8 Hz, CH$_3$), 1.4-1.95 (7H, br m), 3.77 (1H, dd, J=4.9, 2.4 Hz, 8-H), 3.94 (4H, br m, O—CH$_2$CH$_2$—O); $^{13}$C NMR (50 MHz, CDCl$_3$) δ 17.90, 28.50, 30.72, 34.33, 37.03, 64.32, 69.24, 76.01, 109.23; HRMS (ESI) exact mass calcd for C$_9$H$_{16}$O$_3$Na (M$^+$+Na) 195.0997, measured 195.1002.

3 (trans-isomer): $^1$H NMR (200 MHz, CDCl$_3$) δ 1.01 (3H, d, J=6.4 Hz, CH$_3$), 1.54-1.97 (7H, br m), 3.19 (1H, dt, J=4.6, 9.8 Hz, 8-H), 3.93 (4H, br s, O—CH$_2$CH$_2$—O); $^{13}$C NMR (50 MHz, CDCl$_3$) δ 18.49, 29.86, 32.41, 33.41, 37.42, 41.53, 64.48, 75.40, 108.54; HRMS (ESI) exact mass calcd for C$_9$H$_{16}$O$_3$Na (M$^+$+Na) 195.0997, measured 195.0999.

(c) Protection of hydroxy group in 3. trans-7-Methyl-8-pivaloyloxy-1,4-dioxa-spiro[4.5]decane (4). Pivaloyl chloride (2.06 mL, 16.74 mmol) was slowly added to a solution of isomeric alcohols 3 (2.86 g, 16.65 mmol; cis:trans 1:13.3) in anhydrous pyridine (30 mL), and the mixture was stirred at 60° C. for 3 h. Heating bath was removed and the mixture was allowed to cool to the room temperature. A solution of HCl (5%) was then added, and the mixture was extracted with ethyl acetate, washed with saturated NaHCO$_3$, dried over MgSO$_4$, and concentrated. Column chromatography on silica using hexane/ethyl acetate (97:3) gave the ester 4 (3.95 g, 97%); further elution with hexane/ethyl acetate (8:2) provided the unreacted alcohol 3 (cis-isomer, 128 mg).

4: $^1$H NMR (200 MHz, CDCl$_3$) δ 0.90 (3H, d, J=6.6 Hz, CH$_3$), 1.19 (9H, s, t-Bu), 1.43 (1H, br t, J=12.9 Hz), 1.52-1.98 (6H, br m), 3.94 (4H, br s, O—CH$_2$CH$_2$—O), 4.41 (1H, dt, J=4.9, 10.3 Hz, 8-H); $^{13}$C NMR (50 MHz, CDCl$_3$) δ 18.29, 27.33, 28.31, 32.91, 34.63, 39.01, 41.41, 64.51, 64.59, 76.53, 108.23, 178.38; HRMS (ESI) exact mass calcd for C$_{14}$H$_{24}$O$_4$Na (M$^+$+Na) 279.1572, measured 279.1564.

(d) Deprotection of a carbonyl group in the ketal 4. trans-3-Methyl-4-pivaloyloxy-cyclohexanone (5). To a solution of acetal 4 (120 mg, 467.8 μmol) in methylene chloride (13.7 mL) was added FeCl$_3$×6H$_2$O (653 mg, 2.42 mmol) at room temperature. The resulting yellowish suspension was stirred for 1.5 h and quenched by the addition of water. The aqueous layer was extracted with methylene chloride, the combined organic layers were dried over MgSO$_4$ and concentrated. The residue was applied on a silica Sep-Pak cartridge and eluted with hexane/ethyl acetate (98:2) to give ketone 5 (84 mg, 96%) as a colorless oil.

5: $^1$H NMR (200 MHz, CDCl$_3$) δ 1.0 (3H, d, J=6.34 Hz, CH$_3$), 1.23 (9H, s, t-Bu), 1.85 (1H, br m), 2.1-2.6 (6H, br m), 4.84 (1H, dt, J=3.7, 7.8 Hz, 8-H); $^{13}$C NMR (50 MHz, CDCl$_3$) δ 18.40, 27.30, 28.63, 36.79, 38.12, 39.06, 45.79, 73.82, 178.02, 209.57; HRMS (ESI) exact mass calcd for C$_{12}$H$_{20}$O$_3$Na (M$^+$+Na) 235.1310, measured 235.1313.

(e) α-Hydroxylation of the ketone 5. To a stirred solution of ketone 5 (551 mg, 2.59 mmol) and L-proline (143.6 mg, 1.25 mmol) in chloroform (5 mL) a solution of nitrosobenzene (485 mg, 4.53 mmol) in chloroform (10 mL) was slowly added by a syringe pump at 4° C. over 24 h. Then the mixture was stirred at room temperature for additional 2 h. Reaction was quenched by the addition of brine and it was extracted with ethyl acetate, dried over MgSO$_4$ and concentrated. Column chromatography on silica using hexane/ethyl acetate (9:1) gave isomeric α-hydroxy ketones (in the elution order): 6c, 6b and 6a (34.5:30.1:35.4; 380 mg, 64%). The compounds were approx. 90% pure (as judged by NMR) and they were used for the next synthetic steps without further purification.

(2R,4R,5R)-2-Hydroxy-5-methyl-4-pivaloyloxy-cyclohexanone (6a): $^1$H NMR (400 MHz, CDCl$_3$) δ 0.97 (3H, d, J=7.3 Hz, CH$_3$), 1.25 (9H, s, t-Bu), 1.89 (1H, ddd, J=14.4, 11.8, 2.6 Hz, 3α-H), 2.32 (1H, br d, J=13.7 Hz, one of 6-H), 2.54 (2H, m, 3β- and 5β-H), 2.86 (1H, dd, J=13.7, 6.0 Hz, one of 6-H), 3.53 (1H, br s, OH), 4.41 (1H, dd, J=11.8, 7.3 Hz, 2β-H), 5.00 (1H, br s, 4α-H); $^{13}$C NMR (125 MHz, CDCl$_3$) δ 17.5, 27.15, 34.97, 35.79, 36.36, 41.17, 71.84, 72.56, 177.65, 209.13; HRMS (ESI) exact mass calcd for C$_{12}$H$_{20}$O$_4$Na (M$^+$+Na) 251.1260, measured 251.1264.

(2R,4S,5S)-2-Hydroxy-5-methyl-4-pivaloyloxy-cyclohexanone (6b): $^1$H NMR (400 MHz, CDCl$_3$) δ 1.03 (3H, d, J=6.4 Hz, CH$_3$), 1.28 (9H, s, t-Bu), 1.56 (1H, q, J~12 Hz, 3α-H), 2.07 (1H, br m, 5α-H), 2.23 (1H, br t, J~14 Hz, 6β-H), 2.57 (1H, dd, J=14.2, 4.3 Hz, 6α-H), 2.66 (1H, ddd, J=11.8, 6.9, 4.0 Hz, 3β-H), 3.45 (1H, br s, OH), 4.22 (1H, dd, J=12.7, 6.9 Hz, 2β-H), 4.88 (1H, dt, J~4, 11 Hz, 4β-H); $^{13}$C NMR (125 MHz, CDCl$_3$) δ 18.20, 27.05, 38.37, 38.83, 39.36, 43.18, 72.12, 72.37, 177.78, 208.51; HRMS (ESI) exact mass calcd for C$_{12}$H$_{20}$O$_4$Na (M$^+$+Na) 251.1260, measured 251.1261.

(2R,3R,4S)-2-Hydroxy-3-methyl-4-pivaloyloxy-cyclohexanone (6c): $^1$H NMR (400 MHz, CDCl$_3$) δ 0.85 (3H, d, J=7.2 Hz, CH$_3$), 1.26 (9H, s, t-Bu), 2.09 (2H, m), 2.45 (1H, br dd, J=14.2, 4.6 Hz), 2.62 (1H, br m), 2.75 (1H, m), 3.51 (1H, br s, OH), 4.61 (1H, d, J=6.3 Hz, 2β-H), 5.07 (1H, narr m, 4α-H); $^{13}$C NMR (125 MHz, CDCl$_3$) δ 11.10, 26.41, 27.14, 34.54, 38.96, 42.45, 72.85, 74.30, 177.37, 210.65; HRMS (ESI) exact mass calcd for C$_{12}$H$_{20}$O$_4$Na (M$^+$+Na) 251.1260, measured 251.1263.

(f) Protection of hydroxy group in 6a. (2R,4R,5R)-2-[(tert-Butyldiphenylsilyl)oxy]-5-methyl-4-pivaloyloxy-cyclohexanone (7). t-BDPSCl (1.16 mL, 4.53 mmol) was added to a solution of α-hydroxy ketone 6a (765 mg, 3.6 mmol) and silver nitrate (1.72 g, 10.14 mmol) in anhydrous DMF (16 mL) under argon at room temperature; white precipitate formed immediately. Reaction was stirred for 17 h and then it was quenched by the addition of water. The mixture was extracted with hexane, dried over MgSO$_4$, and concentrated. Purification by column chromatography on silica (1%→4% diethyl ether/hexane) gave protected α-hydroxy ketone 7 (1.2 g, 97%).

7: [α]$^{20}_D$ −61° (c 1.7, CHCl$_3$); $^1$H NMR (400 MHz, CDCl$_3$) δ 0.98 (3H, d, J=7.1 Hz, CH$_3$), 1.06 (9H, s, Si-t-Bu), 1.10 (9H, s, t-Bu), 1.98 (1H, dt, J~13.5, 5 Hz, 3β-H), 2.13 (1H, ddd, J=13.4, 9.6, 3.5 Hz, 3α-H), 2.23 (1H, m, 5β-H), 2.32 (1H, dd, J=13.2, 5.0 Hz, 6α-H), 2.48 (1H, dd, J=13.2, 5.4 Hz, 6β-H), 4.29 (1H, dd, J=9.6, 5.7 Hz, 2β-H), 4.97 (1H, dt, J=3.5, 4.5 Hz, 4α-H), 7.37 (6H, m, Ar—H), 7.67 (4H, m, Ar—H); $^{13}$C NMR (100 MHz, CDCl$_3$) δ 14.15, 17.7, 19.27, 26.83, 26.97, 36.73, 37.25, 38.68, 42.42, 72.71, 73.85, 127.60, 127.67, 129.77, 129.84, 132.88, 133.30, 135.71, 135.78, 177.23, 207.43; HRMS (ESI) exact mass calcd for $C_{28}H_{38}O_4SiNa$ (M$^+$+Na) 489.2437, measured 489.2435.

(g) Wittig methylenation of the ketone 7. (2R,4R,5R)-2-[(tert-Butyldiphenylsilyl)oxy]-5-methyl-1-methylene-4-pivaloyloxy-cyclohexane (8). To methyltriphenylphosphonium bromide (122 mg, 342 µmol) in anhydrous THF (1.4 mL) at 0° C. was added dropwise n-BuLi (1.6 M in hexanes; 431 µL, 689.5 µmol). After 15 min another portion of phosphonium salt (122 mg, 342 mop was added, and the solution was stirred at 0° C. for 10 min, and at room temperature for 20 min. The orange-red mixture was then cooled to −78° C. and siphoned to the precooled (−78° C.) solution of the ketone 7 (160 mg, 344 µmol) in anhydrous THF (350 µL). The reaction mixture was stirred at −78° C. for 4 h and then at room temperature for 1 h. The mixture was poured into brine and extracted with hexane. The organic layer was dried over MgSO$_4$ and evaporated to give an orange oily residue which was applied on a silica Sep-Pak cartridge. Elution with hexane/diethyl ether (97:3) gave pure olefinic compound 8 (153 mg, 97%) as a colorless oil.

8: $[\alpha]^{20}_D$ −47° (c 2.83, CHCl$_3$); $^1$H NMR (400 MHz, CDCl$_3$) δ 0.96 (3H, d, J=6.7 Hz, CH$_3$), 1.08 (9H, s, Si-t-Bu), 1.10 (9H, s, t-Bu), 1.43 (1H, ddd, J=13.0, 8.2, 3.5 Hz, 3β-H), 1.75 (1H, m, 5β-H), 1.94 (1H, ddd, J=13.0, 6.3, 3.8 Hz, 3α-H), 2.26 (2H, d, J=6.5 Hz, 6-H$_2$), 4.29 (1H, dd, J=6.3, 3.5 Hz, 2β-H), 4.69 and 4.76 (1H and 1H, each s, =CH$_2$), 4.96 (1H, dt, J=3.8, 8.2 Hz, 4α-H), 7.36 (6H, m, Ar—H), 7.68 (4H, m, Ar—H); $^{13}$C NMR (100 MHz, CDCl$_3$) δ 17.6, 19.32, 26.95, 27.10, 36.48, 36.65, 38.59, 38.70, 72.46, 74.20, 108.97, 127.41, 127.53, 129.51, 129.59, 133.71, 134.06, 135.87, 135.92, 147.31, 177.53; HRMS (ESI) exact mass calcd for $C_{29}H_{40}O_3SiNa$ (M$^+$+Na) 487.2645, measured 487.2664.

(h) Reduction of the ester 8. (1R,2R,5R)-5-[(tert-Butyldiphenylsilyl)oxy]-2-methyl-4-methylene-cyclohexanol (9). Diisobutylaluminium hydride (1.0 M in toluene; 6.12 mL, 6.12 mmol) was slowly added to a stirred solution of ester 8 (710 mg, 1.53 mmol) in toluene:methylene chloride (2:1, 45 mL) at −78° C. under argon. Stirring was continued at −78° C. for 1 h and at −40° C. for 30 min. The mixture was quenched by the addition of potassium-sodium tartrate (2N, 4 mL), aqueous HCl (2N, 4 mL) and H$_2$O (14 mL), and extracted with ethyl acetate. The organic phase was washed with brine, dried over MgSO$_4$ and evaporated. The residue was purified by column chromatography on silica using hexane/ethyl acetate (9:1) gave alcohol 9 (558 mg, 96%).

9: $[\alpha]^{20}_D$ −42° (c 4.0, CHCl$_3$); NMR (200 MHz, CDCl$_3$) δ 1.06 (9H, s, Si-t-Bu), 1.07 (3H, d, J=6.2 Hz, CH$_3$), 1.34 (1H, J=12.8, 10.2, 3.0 Hz, 6β-H), 1.47 (1H, m, 2β-H), 2.04 (1H, dt, J=12.8, 4.4 Hz, 6α-H), 2.13-2.35 (2H, m, 3-H$_2$), 3.83 (1H, dt, J~4, 10 Hz, 1α-H), 4.32 (1H, narr m, 5β-H), 4.51 and 4.63 (1H and 1H, each s, =CH$_2$), 7.37 (6H, m, Ar—H), 7.65 (4H, m, Ar—H); $^{13}$C NMR (50 MHz, CDCl$_3$) main signals: δ18.45, 19.49, 27.16, 36.88, 40.97, 43.27, 72.27, 73.82, 109.52, 127.58, 127.78, 129.77, 129.85, 134.01, 134.48, 135.99, 136.16, 148.23; HRMS (ESI) exact mass calcd for $C_{24}H_{32}O_2SiNa$ (M$^+$+Na) 403.2070, measured 403.2064

(i) Oxidation of the cyclohexanol 9. (2R,5R)-5-[(tert-Butyldiphenylsilyl)oxy]-2-methyl-4-methylene-cyclohexanone (10). To a stirred solution of alcohol 9 (396 mg, 1.04 mmol) in anhydrous methylene chloride (20 mL) was added Dess-Martin periodinane (529 mg, 1.25 mmol) at room temperature under argon. Stirring was continued for 1 h and saturated NaHCO$_3$ was slowly added. The mixture was extracted with methylene chloride, dried over MgSO$_4$ and concentrated. The residue was applied on a silica Sep-Pak cartridge and eluted with hexane/diethyl ether (98:2) to afford ketone 10 (389 mg, 95%) as a colorless oil.

10: $[\alpha]^{20}_D$ −49° (c 3.0, CHCl$_3$); $^1$H NMR (200 MHz, CDCl$_3$) δ 1.02 (9H, s, Si-t-Bu), 1.13 (3H, d, J=6.2 Hz, CH$_3$), 2.35-2.72 (5H, br m), 4.52 (1H, t, J=3.5 Hz, 5β-H), 4.71 and 4.84 (1H and 1H, each br s, =CH$_2$), 7.37 (6H, m, Ar—H), 7.64 (4H, m, Ar—H); $^{13}$C NMR (50 MHz, CDCl$_3$) δ15.04, 19.43, 27.01, 37.96, 45.59, 50.37, 75.52, 110.99, 127.86, 129.91, 130.03, 133.52, 133.71, 136.04, 136.02, 146.51, 210.37; HRMS (ESI) exact mass calcd for $C_{24}H_{30}O_2SiNa$ (M$^+$+Na) 401.1913, measured 401.1899.

(j) Conversion of the ketone 10 into hydroxyalkyne 11. (1S,2R,5R)-5-[(tert-Butyldiphenylsilyl)oxy]-2-methyl-4-methylene-1-[(trimethylsilanyl)ethynyl]-cyclohexanol (11). A solution of n-BuLi (1.6 M in hexanes, 326 µL, 522 µmol) was added dropwise to a solution of trimethylsilylacetylene (76 µL, 537 µmol) in anhydrous THF (2 mL) under argon at 0° C. The solution was stirred for 30 min and cooled to −78° C., then precooled (−78° C.) solution of ketone 10 (158 mg, 417.3 µmol) in dry THF (2 mL) was slowly added. After 15 min the mixture was warmed to 0° C., and stirred for additional 30 min. Reaction was quenched by the addition of water, extracted with ether, dried over MgSO$_4$, and concentrated. The resulting product was applied on a silica Sep-Pak cartridge and eluted with hexane/ethyl acetate (98:2) to afford alcohol 11 (190 mg, 96%) as a colorless oil.

11: $[\alpha]^{20}_D$ −42° (c 1.6, CHCl$_3$); $^1$H NMR (200 MHz, CDCl$_3$) δ 0.16 (9H, s, 3×SiCH$_3$), 1.06 (9H, s, Si-t-Bu), 1.16 (3H, d, J=6.8 Hz, CH$_3$), 1.76 (1H, m, 2β-H), 1.78 (1H, dd, J=14.0, 2.9 Hz, 6β-H), 2.07 (1H, dd, J=14.0, 4.2 Hz, 6α-H), 2.38-2.52 (2H, m, 3-H$_2$), 4.23 (1H, br s, one of =CH$_2$), 4.32 (1H, br t, J=3 Hz, 5β-H), 4.51 (1H, br s, OH), 4.57 (1H, t, J=2 Hz, one of =CH$_2$), 7.39 (6H, m, Ar—H), 7.65 (4H, m, Ar—H); $^{13}$C NMR (50 MHz, CDCl$_3$) δ −0.02, 15.86, 19.10, 26.92, 33.84, 43.18, 45.07, 70.64, 74.48, 108.69, 110.61, 127.47, 127.76, 129.83, 129.97, 132.50, 132.82, 135.84, 136.13, 146.39; HRMS (ESI) exact mass calcd for $C_{29}H_{40}O_2Si_2Na$ (M$^+$+Na) 499.2465, measured 499.2473.

(k) Dehydration of the alcohol 11. (5R)-5-[(tert-Butyldiphenylsilyl)oxy]-2-methyl-4-methylene-1-[(trimethylsilanyl)ethynyl]-cyclohexene (12). Mesyl chloride (170 µL, 2.19 mmol) was slowly added to a stirred solution of alcohol 11 (174 mg, 364 µmol) and TEA (309 µL, 2.21 mmol) in dry methylene chloride (6 mL) at room temperature under argon. The reaction was quenched after 1 h by the addition of 5% HCl and it was extracted with methylene chloride. The organic phase was washed with saturated NaHCO$_3$, dried over MgSO$_4$ and concentrated. The resulting product was applied on a silica Sep-Pak cartridge and eluted with hexane/diethyl ether (99:1) to afford enyne 12 (64 mg, 38%) as a colorless oil.

12: $^1$H NMR (200 MHz, CDCl$_3$) δ 0.16 (9H, s, 3×SiCH$_3$), 1.07 (9H, s, Si-t-Bu), 1.86 (3H, s, CH$_3$), 2.28 (2H, m, 6-H$_2$), 2.73 and 2.95 (1H and 1H, each br d, J=19.8 Hz, 3-H$_2$), 4.32 (1H, t, J=6.5 Hz, 5β-H), 4.77 and 5.05 (1H and 1H, each s, =CH$_2$), 7.38 (6H, Ar—H), 7.67 (4H, m, Ar—H); $^{13}$C NMR (50 MHz, CDCl$_3$) δ 0.17, 19.38, 21.28, 26.97, 38.86, 40.43, 70.89, 95.46, 105.22, 106.93, 112.11, 127.57, 129.65, 133.80, 134.29, 135.78, 135.86, 141.76, 145.85; HRMS (ESI) exact mass calcd for $C_{29}H_{38}OSi_2Na$ (M$^+$+Na) 481.2359, measured 481.2361.

(l) Removal of TMS group from 12. (5R)-5-[(tert-Butyldiphenylsilyl)oxy]-1-ethynyl-2-methyl-4-methylene-cyclohexane (13). Anhydrous potassium carbonate (34.5 mg, 250 µmol) was added to the stirred solution of protected acetylene (58 mg, 126 µmol) in anhydrous THF/MeOH (1:1, 6 mL) at room temperature under argon. The stirring was continued for 19 h, then water and saturated $NH_4Cl$ were added, the mixture was extracted with hexane, dried over $MgSO_4$ and concentrated. The residue was applied on a silica Sep-Pak cartridge and eluted with hexane to afford compound 13 (47 mg, 96%).

13: $^1H$ NMR (200 MHz, $CDCl_3$) δ 1.07 (9H, s, Si-t-Bu), 1.86 (3H, s, $CH_3$), 2.29 (2H, m, 6-$H_2$), 2.74 and 2.96 (1H and 1H, each br d, J=19.6 Hz, 3-$H_2$), 2.96 (1H, s, ≡CH), 4.33 (1H, t, J=6.3 Hz, 5β-H), 4.78 and 5.05 (1H and 1H, each s, =$CH_2$), 7.38 (6H, 7.67 (4H, m, Ar—H); $^{13}C$ NMR (50 MHz, $CDCl_3$) δ 19.36, 21.13, 26.95, 38.72, 40.49, 70.82, 78.72, 83.95, 107.13, 111.01, 127.55, 127.59, 129.62, 129.69, 135.78, 135.82, 142.00, 145.73; HRMS (ESI) exact mass calcd for $C_{26}H_{30}OSiNa$ ($M^+$+Na) 409.1964, measured 409.1954.

(m) Coupling of dienyne 13 with the triflate 14 (SCHEME II). 3β-[(tert-Butyldiphenylsilyl)oxy]-2-methylene-25-[(triethylsilyl)oxy]-9,10-secocholesta-5(10),8-dien-6-yne (15). To a solution of acetylene 13 (47 mg, 121.6 µmol) and triflate 14 (50 mg, 95 µmol) in anhydrous DMF (0.95 mL) were added CuI (2.7 mg, 14.2 µmol), $(PPh_3)_2Pd(OAc)_2$ (2.0 mg, 2.7 µmol) and $Et_2NH$ (945 µL) at room temperature under argon. After 20 min the mixture turned deep reddish-brown. Water was added and the mixture was extracted with hexane, dried over $MgSO_4$ and concentrated. The resulting product was applied on a silica Sep-Pak cartridge and eluted with hexane to afford compound 15 (63 mg, 87%).

15: $^1H$ NMR (200 MHz, $CDCl_3$; vitamin D numbering) δ 0.56 (6H, q, J=7.6 Hz, 3×$SiCH_2$), 0.76 (3H, s, 18-$H_3$), 0.93 (3H, d, J=7 Hz, 21-$H_3$), 0.95 (9H, t, J=7.6 Hz, 3×$SiCH_2CH_3$), 1.07 (9H, s, Si-t-Bu), 1.19 (6H, s, 26- and 27-$H_3$), 1.83 (3H, s, 19-$H_3$), 2.23 (2H, m), 2.74 and 2.95 (1H and 1H, each br d, J=19.6 Hz, 1-$H_2$), 4.34 (1H, t, J=6.2 Hz, 3α-H), 4.78 and 5.07 (1H and 1H, each s, =$CH_2$), 5.88 (1H, narr m, 9-H), 7.38 (6H, m, Ar—H), 7.67 (4H, m, Ar—H); HRMS (ESI) exact mass calcd for $C_{50}H_{74}O_2Si_2Na$ ($M^+$+Na) 785.5125, measured 785.5150.

(n) Hydrogenation of the trienyne 15 and thermal reaction of previtamin D compound 16. 2-Methylene-25-[(triethylsilyl)oxy]-vitamin $D_3$ tert-butyldiphenylsilyl ether (17). To a solution of the trienyne 15 (63 mg, 82.5 µmol) in hexane (7.6 mL) and quinoline (13.5 µL) was added Lindlar catalyst (189 mg) and the mixture was stirred at room temperature under a positive pressure of hydrogen. Lindlar catalyst was added four times during 8 h (in 30 mg portions) and then the mixture was applied on a silica Sep-Pak cartridge and eluted with hexane/ether (99.7:0.3) to yield a mixture of previtamin D product and unreacted substrate. Further purification by preparative TLC (Silica Gel 60$F_{254}$, 20×20 cm, 250 µm layer) with hexane/ether (98:2) gave the previtamin compound 16 (12.7 mg, 20%; 25% based on recovered substrate) and 12.1 mg of the unchanged dienyne. Silylated previtamin was then dissolved in anhydrous hexane (6 mL) and stirred at 65° C. for 5 h and at 40° C. overnight under argon. Solvent was evaporated and residue was purified by HPLC (9.4 mm×25 cm Zorbax-Sil column, 4 mL/min) using hexane/ethyl acetate (99:1) solvent system. Pure protected vitamin 17 (9.7 mg, 76%) was eluted at $R_V$ 15.5 mL.

17: $^1H$ NMR (200 MHz, $CDCl_3$) δ 0.520 (3H, s, 18-$H_3$), 0.557 (6H, q, J=7.6 Hz, 3×$SiCH_2$), 0.875 (3H, d, J=6.0 Hz, 21-$H_3$), 0.941 (9H, t, J=7.6 Hz, 3×$SiCH_2CH_3$), 1.072 (9H, s, Si-t-Bu), 1.184 (6H, s, 26- and 27-$H_3$), 2.73 (1H, br d, J=12.5 Hz, 9β-H), 2.77 and 3.15 (1H and 1H, each br d, J=13.5 Hz, 1-$H_2$), 4.27 (1H, t, J=6.5 Hz, 3α-H), 4.75, 4.79, 5.00 and 5.02 (each 1H, each s, 2×=$CH_2$), 5.95 and 6.01 (1H and 1H, each d, J=11.0 Hz, 1- and 6-H), 7.39 (6H, m, Ar—H), 7.69 (4H, m, Ar—H); HRMS (ESI) exact mass calcd for $C_{50}H_{76}O_2Si_2Na$ ($M^+$+Na) 787.5281, measured 787.5272.

(o) Deprotection of hydroxyls in the vitamin D compound 17. 25-Hydroxy-2-methylene-vitamin $D_3$ (18). To a solution of protected vitamin 17 (8.7 mg) in THF (0.7 mL) was added tetrabutylammonium fluoride (1.0 M in THF; 546 µL, 546 µmol) at room temperature under argon. The stirring was continued for 18 h, brine was added and the mixture was extracted with ethyl acetate. The organic extracts were dried over $MgSO_4$ and evaporated. The residue was purified by HPLC (9.4 mm×25 cm Zorbax-Sil column, 4 mL/min) using hexane/2-propanol (97:3) solvent system; vitamin 18 (1.357 mg, 29%) was collected at $R_V$ 35 mL. Analytical sample of the vitamin was obtained after HPLC (9.4 mm×25 cm Zorbax Eclipse XDB-C18 column, 4 mL/min) using methanol/water (93:7) solvent system ($R_V$ 28 mL).

18: UV (EtOH) $\lambda_{max}$ 268.5 nm; $^1H$ NMR (500 MHz, $CDCl_3$) δ 0.552 (3H, s, 18-$H_3$), 0.939 (3H, d, J=6.5 Hz, 21-$H_3$), 1.219 (6H, s, 26- and 27-$H_3$), 2.35 (1H, dd, J=13.0, 7.5 Hz, 4β-H), 2.63 (1H, dd, J=13.0, 3.5 Hz, 4α-H), 2.83 (1H, br d, J~13 Hz, 9β-H), 2.89 and 3.14 (1H and 1H, each d, J=14.5 Hz, 1-$H_2$), 4.13 (1H, m, 3α-H), 4.84, 4.96 and 5.07 (2H, 1H and 1H, each s, 2×=$CH_2$), 6.08 and 6.32 (1H and 1H, each d, J=11.0 Hz, 7- and 6-H); HRMS (ESI) exact mass calculated for $C_{28}H_{44}O_2Na$ ($M^+$+Na) 435.3239. found 435.3231.

Example II

Preparation of (20S)-25-hydroxy-2-methylene-vitamin $D_3$ (32)

(a) Dehydration of the hydroxy ester 20 (SCHEME III). (5R)-5-[(tert-Butyldimethylsilyl)oxy]-4-methylene-cyclohex-1-enecarboxylic acid methyl ester (21) To the solution of alcohol 20 (162.5 mg, 540.8 µmol) in anhydrous carbon tetrachloride (5.1 mL) at room temperature under argon was added solution of [α,α-bis(trifluoromethyl)benzenemethanolato]diphenylsulfur (545.6 mg, 811.2 µmol) in anhydrous carbon tetrachloride (1.8 mL). Reaction was stirred for 2 h and water was added. The mixture was extracted with methylene chloride, dried over $Na_2SO_4$ and concentrated. The resulting product was applied on a silica Sep-Pak cartridge and eluted with hexane/diethyl ether (97:3) to give the desired product contaminated by dehydrating reagent. Further purification on preparative TLC plates (Silica Gel 60$F_{254}$, 20×20 cm, layer thickness 250 nm) using hexane/diethyl ether (92:8) afforded unsaturated ester 21 (139 mg, 91%) as a colorless oil.

21: $[α]_D$ –48° (c 1.0, $CHCl_3$); $^1H$ NMR (500 MHz, $CDCl_3$) δ 0.065 and 0.083 (3H and 3H, each s, 2×$SiCH_3$), 0.902 (9H, s, Si-t-Bu), 2.34 (1H, dm, J=17.0 Hz, 6α-H), 2.69 (1H, br dd, J=17.0, 6.0 Hz, 6β-H), 2.97 and 3.10 (1H and 1H, each br d, J=21.0 Hz, 3α- and 3β-H), 3.73 (3H, s, COOCH$_3$), 4.34 (1H, t, J=6.5 Hz, 5β-H), 4.84 and 5.08 (1H and 1H, each s, =$CH_2$), 6.88 (1H, s, 2-H); $^{13}C$ NMR (125 MHz, $CDCl_3$) δ –4.99, –4.96, 18.24, 25.76, 33.01, 35.91, 51.67, 69.96, 107.49, 127.81, 137.85, 145.25, 167.28; HRMS (ESI) exact mass calculated for $C_{15}H_{26}O_3SiNa$ ($M^+$+Na) 305.1549. found 305.1558.

(b) Addition of diazomethane to the ester 21. (3aR,6R,7aR)-6-[(tert-Butyldimethylsilyl)oxy]-5-methylene-3,3a,4, 5,6,7-hexahydro-indazole-7a-carboxylic acid methyl ester (22). Solution of diazomethane in diethyl ether [5.5 mL; prepared according to the procedure of Arndt, Org. Synth., 15, 3 and 48 (1935)] was added to the solution of unsaturated ester 21 (375 mg, 1.327 mmol) in anhydrous diethyl ether (2 mL) at room temperature. Reaction mixture was protected from light and stirred overnight. Solvent was evaporated, a residue dissolved in hexane, applied on a silica Sep-Pak cartridge and eluted with hexane/ethyl acetate (96:4) to give bicyclic compound 22 (423 mg, 99%) as a colorless oil.

22: $[\alpha]_D$+2.1° (c 1.0, CHCl$_3$); $^1$H NMR (400 MHz, CDCl$_3$) δ 0.071 and 0.092 (3H and 3H, each s, 2×SiCH$_3$), 0.892 (9H, s, Si-t-Bu), 1.14 (1H, dd, J=13.2, 11.0 Hz), 2.41 (3H, br m), 2.70 (1H, dd, J=8.8, 4.4 Hz), 3.83 (3H, s, COOCH$_3$), 3.98 (1H, dd, J=17.0, 9.2 Hz, one of =N—CH$_2$), 4.26 (1H, dd, J=10.4, 4.0 Hz, 6β-H), 4.75 (1H, dd, J=17.0, 7.6 Hz, one of =N—CH$_2$), 4.86 and 5.13 (1H and 1H, each s, =CH$_2$); $^{13}$C NMR (100 MHz, CDCl$_3$) α −5.16, −5.08, 18.17, 25.67, 29.99, 36.48, 38.36, 52.86, 68.67, 79.42, 92.77, 109.52, 144.8, 171.33; HRMS (ESI) exact mass calculated for C$_{16}$H$_{28}$N$_2$O$_3$SiNa (M$^+$+Na) 347.1767. found 347.1758.

(c) Pyrolysis of the adduct 22. (5R)-5-[(tert-Butyldimethylsilyl)oxy]-2-methyl-4-methylene-cyclohex-1-enecarboxylic acid methyl ester (23). A solution of compound 22 (310 mg, 955 μmol) in freshly distilled anhydrous DMSO (16 mL) was stirred at 125° C. under argon for 5 h. Heating bath was removed, water added and the mixture was extracted with hexane, dried over Na$_2$SO$_4$ and concentrated. Column chromatography on silica using hexane/diethyl ether (97:3) gave unsaturated ester 23 (239 mg, 98%) and recovered substrate (43 mg).

23: $[\alpha]_D$−41° (c 1.0, CHCl$_3$); $^1$H NMR (400 MHz, CDCl$_3$) δ 0.067 and 0.078 (3H and 3H, each s, 2×SiCH$_3$), 0.907 (9H, s, Si-t-Bu), 2.03 (3H, s, CH$_3$), 2.32 (1H, br m, 6α-H), 2.67 (1H, br dd, J=16.4, 5.2 Hz, 6β-H), 2.97 (2H, s, 3α- and 3β-H), 3.72 (3H, s, COOCH$_3$), 4.30 (1H, t, J=6.8 Hz, 5β-H), 4.78 and 5.03 (1H and 1H, each s, =CH$_2$); $^{13}$C NMR (100 MHz, CDCl$_3$) δ −4.96, 18.24, 21.02, 25.79, 37.79, 41.14, 51.22, 70.04, 106.15, 121.54, 145.59, 145.93, 168.33; HRMS (ESI) exact mass calculated for C$_{16}$H$_{28}$O$_3$SiNa (M$^+$+Na) 319.1706. found 319.1705.

(d) Reduction of the ester 23. (5'R)-5'-[(tert-Butyldimethylsilyl)oxy]-2'-methyl-4'-methylene-cyclohex-1'-enyl)-methanol (24). Diisobutylaluminum hydride (1.0 M in toluene; 1.33 mL, 1.33 mmol) was slowly added to a stirred solution of the ester 23 (89 mg, 300 μmol) in toluene/methylene chloride (2:1; 8 mL) at −78° C. under argon. Stirring was continued at −78° C. for 1 h. The mixture was quenched by slow addition of potassium-sodium tartrate (2N, 4 mL), aqueous HCl (2N, 4 mL), H$_2$O and extracted with ethyl acetate. The combined organic layers were washed with brine, dried (MgSO$_4$) and concentrated. The residue was applied on a silica Sep-Pak cartridge and eluted with hexane/ethyl acetate (95:5) to afford the alcohol 24 (78 mg, 96%).

24: $[\alpha]_D$−49° (c 1.0, CHCl$_3$); $^1$H NMR (500 MHz, CDCl$_3$) δ 0.074 and 0.079 (3H and 3H, each s, 2×SiCH$_3$), 0.914 (9H, s, Si-t-Bu), 1.702 (3H, s, CH$_3$), 2.19 (1H, m, 6'α-H), 2.51 (1H, br dd, J=15.5, 5.0 Hz, 6'β-H), 2.80 and 2.86 (1H and 1H, each d, J=19.0 Hz, 3'α- and 4.04 and 4.11 (1H and 1H, each d, J=11.5 Hz, CH$_2$OH), 4.33 (1H, t, J=7.5 Hz, 5'β-H), 4.76 and 5.03 (1H and 1H, each s, =CH$_2$); $^{13}$C NMR (125 MHz, CDCl$_3$) δ −4.98, −4.93, 17.91, 18.28, 25.81, 39.31, 39.79, 62.43, 70.75, 105.33, 127.32, 129.77, 147.49; HRMS (ESI) exact mass calculated for C$_{15}$H$_{28}$O$_2$SiNa (M$^+$+Na) 291.1757. found 291.1749.

(e) Oxidation of alcohol 24. (5'R)-5'-[(tert-Butyldimethylsilyl)oxy]-2-methyl-4-methylene-cyclohex-1-enecarbaldehyde (25). The mixture of alcohol 24 (77 mg, 286.8 μmol), and pyridinium dichromate (347 mg, 1.61 mmol) in anhydrous methylene chloride (4.6 mL) was stirred vigorously at room temperature under argon for 16 h. Then the reaction mixture was filtered through a pad of Celite (washed with methylene chloride) and solvent was removed under reduced pressure. The residue was applied on a silica Sep-Pak cartridge and eluted with hexane/ethyl acetate (98:2) to yield the aldehyde 25 (33.5 mg, 44%) as a colorless oil.

25: $[\alpha]_D$−49° (c 1.0, CHCl$_3$); $^1$H NMR (500 MHz, CDCl$_3$) δ 0.060 and 0.074 (3H and 3H, each s, 2×SiCH$_3$), 0.892 (9H, s, Si-t-Bu), 2.16 (3H, s, CH$_3$), 2.23 (1H, ddd, J=16.5, 7.5, 1.5 Hz, 6α-H), 2.64 (1H, br dd, J=16.5, 5.5 Hz, 6β-H), 3.02 and 3.13 (1H and 1H, each br d, J=21.0 Hz, 3'α- and 3'β-H), 4.30 (1H, ~t, J=6.5 Hz, 5β—H), 4.82 and 5.07 (1H and 1H, each s, =CH$_2$), 10.09 (1H, s, CHO); $^{13}$C NMR (125 MHz, CDCl$_3$) δ −4.96, −4.94, 17.48, 18.23, 25.76, 33.81, 41.11, 69.91, 107.17, 131.25, 145.29, 154.11, 190.46; HRMS (ESI) exact mass calculated for C$_{15}$H$_{26}$O$_2$SiNa (M$^+$+Na) 289.1600. found 289.1608.

(f) Transformation of the aldehyde 25 to the dienyne 26. (5'R)-5'-[(tert-Butyldimethylsilyl)oxy]-1-ethynyl-2-methyl-4-methylene-cyclohexene (26). n-BuLi (1.6 M in hexanes; 101 μL, 161.71 μmol) was added to a solution of (trimethylsilyl)diazomethane (2.0 M in hexane, 76 μL, 151.52 μmol) in anhydrous THF (150 μL) at −78° C. under argon, and a solution of aldehyde 25 (33.5 mg, 125.73 μmol) in dry THF (100 μL+100 μL) was added via cannula. After 1 h the cooling bath was removed and stirring was continued at room temperature overnight. Water was added and the mixture was extracted with hexane, dried over Na$_2$SO$_4$ and concentrated. The residue was applied on a silica Sep-Pak cartridge and eluted with hexane to afford the dienyne 26 (16 mg, 52%) and recovered substrate (1.5 mg).

26: $[\alpha]_D$−44.5° (c 1.0, CHCl$_3$); $^1$H NMR (500 MHz, CDCl$_3$) δ 0.067 and 0.075 (3H and 3H, each s, 2×SiCH$_3$), 0.907 (9H, s, Si-t-Bu), 1.89 (3H, s, CH$_3$), 2.26 (1H, br m, 6α-H), 2.48 (1H, dd, J=16.0, 5.5 Hz, 6β-H), 2.88 and 2.92 (1H and 1H, each d, J=23.0 Hz, 3α- and 3β-H), 3.03 (1H, s, ≡CH), 4.30 (1H, ~t, J=7.0 Hz, 3α-H), 4.79 and 5.04 (1H and 1H, each s, =CH$_2$); $^{13}$C NMR (125 MHz, CDCl$_3$) δ −4.98, −4.93, 18.27, 21.09, 25.79, 39.01, 40.75, 69.85, 78.80, 83.59, 106.32, 111.16, 142.08, 146.17; HRMS (ESI) exact mass calculated for C$_{16}$H$_{26}$OSiNa (M$^+$+Na) 285.1651. found 285.1648.

(g) Conversion of the Grundmann ketone 27 to the enol triflate 28 (SCHEME IV). (20S)-25-[(Triethylsilyl)oxy]-8-trifluoromethanesulfonyloxy-des-A,B-cholest-8-ene (28). A solution of the ketone 27 (28.5 mg, 72.19 μmol) in anhydrous THF (350 μL) was slowly added to the solution of LDA (2.0 M in THF/heptane/ethylbenzene; 40 μL, 80 μmol) in dry THF (100 μL) at −78° C. under argon. Then a solution of N-phenyltriflimide (28.3 mg, 79.27 μmol) in dry THF (100 μL) was added. After 2 h cooling bath was removed and reaction mixture was allowed to warm up to room temperature. Stirring was continued for 30 min and water was added. The mixture was extracted with hexane, dried over MgSO$_4$ and concentrated. The residue was applied on a silica Sep-Pak cartridge and eluted with hexane to afford the enol triflate 28 (17.2 mg, 82% considering recovered substrate) and unreacted ketone 27 (12 mg).

28: $[\alpha]^{20}_D$−5.3° (c 0.86 CHCl$_3$); $^1$H NMR (200 MHz, CDCl$_3$) δ 0.564 (6H, q, J=8 Hz, 3×SiCH$_2$), 0.762 (3H, s, 18-H$_3$), 0.855 (3H, d, J=6.4 Hz, 21-H$_3$), 0.944 (9H, t, J=7.6 Hz, 3×SiCH$_2$CH$_3$), 1.18 (6H, s, 26- and 27-H$_3$), 1.789 (1H, m), 1.97 (2H, m), 2.30 (2H, m), 2.48 (1H, m), 5.66 (1H, dd, J=6.8, 3.4 Hz, 9-H); $^{13}$C NMR (50 MHz, CDCl$_3$) δ 6.98, 7.30, 11.68, 18.74, 20.83, 21.54, 24.07, 28.43, 30.02, 30.11, 35.01, 35.68, 35.94, 45.62, 50.36, 54.03, 73.54, 116.18, 150.16; HRMS (ESI) exact mass calculated for C$_{25}$H$_{45}$F$_3$O$_4$SSiNa (M$^+$+Na) 549.2658. found 549.2637.

(h) Coupling of dienyne 26 with the triflate 28. (20S)-3β-[(tert-Butyldimethylsilyl)oxy]-2-methylene-25-[(triethylsilyl)oxy]-9,10-secocholesta-5(10),8-dien-6-yne (29). To a solution of dienyne 26 (6.1 mg, 22.9 μmol) and triflate 28 (8.9 mg, 16.89 μmol) in anhydrous DMF (200 μL) were added CuI (0.507 mg, 2.66 μmol), (PPh$_3$)$_2$Pd(OAc)$_2$ (0.38 mg, 0.507 μmol) and Et$_2$NH (185 μL) at room temperature under argon. After 30 min the mixture turned deep reddish-brown. Water was added and the mixture was extracted with hexane, dried over MgSO$_4$ and concentrated. The resulting product was applied on a silica Sep-Pak cartridge and eluted with hexane to afford trienyne 29 (10 mg, 93%).

29: $^1$H NMR (200 MHz, CDCl$_3$) δ 0.071 (6H, s, 2×SiCH$_3$), 0.561 (6H, q, J=7.8 Hz, 3×SiCH$_2$), 0.705 (3H, s, 18-H$_3$), 0.908 (9H, s, Si-t-Bu), 0.944 (9H, t, J=7.8 Hz, 3×SiCH$_2$CH$_3$), 1.18 (6H, s, 26- and 27-H$_3$), 1.87 (3H, s, CH$_3$), 2.47 (1H, dd, J=13.4, 4.6 Hz), 4.29 (1H, t, J~8.0 Hz, 3α-H), 4.78 and 5.04 (1H and 1H, each s, =CH$_2$), 5.95 (1H, narr m, 9-H); HRMS (ESI) exact mass calculated for C$_{40}$H$_{70}$O$_2$Si$_0$Na (M$^+$+Na) 661.4813. found 661.4823.

(i) Hydrogenation of the trienyne 29 and thermal reaction of previtamin D compound 30. (20S)-2-Methylene-25-[(triethylsilyl)oxy]-vitamin D$_3$ tert-butyldiphenylsilyl ether (31). To a solution of the trienyne 29 (10 mg, 15.64 μmol) in hexane (1.8 mL) and quinoline (2.61 μL) was added Lindlar catalyst (36.46 mg) and the mixture was stirred at room temperature under a positive pressure of hydrogen. Lindlar catalyst was added twice during 2 h (in 20 mg portions) and then the mixture was applied on a silica Sep-Pak cartridge and eluted with hexane/ether (99:1) to give the silylated previtamin 30 (8 mg, 80%). The previtamin was then dissolved in anhydrous hexane (5 mL) and stirred at 60° C. for 8 h and overnight under argon. Solvent was evaporated and residue was applied on a silica Sep-Pak cartridge and eluted with hexane/diethyl ether (99.8:0.2) to give protected vitamin 31 (7 mg, 87%).

31: $^1$H NMR (200 MHz, CDCl$_3$) δ 0.070 (6H, s, 2×SiCH$_3$), 0.553 (3H, s, 18-H$_3$), 0.556 (6H, q, J=7.5 Hz, 3×SiCH$_2$), 0.864 (3H, d, J=6.5 Hz, 21-H$_3$), 0.907 (9H, s, Si-t-Bu), 0.943 (9H, t, J=7.5, 3×SiCH$_2$CH$_3$), 1.187 (6H, s, 26- and 27-H$_3$), 2.26 (1H, br m, 4β-H), 2.48 (1H, dd, J=16.0, 4.9 Hz, 4α-H), 2.81 (1H, br d, J=14 Hz, 9β-H), 2.88 and 2.92 (1H and 1H, each d, J=14.0 Hz, 1α- and 1β-H), 4.20 (1H, dd, J=9.6, 3.8 Hz, 3α-H), 4.78, 4.99 and 5.03 (2H, 1H and 1H, each s, 2×=CH$_2$), 6.01 and 6.23 (1H and 1H, each d, J=11.0 Hz, 7- and 6-H); HRMS (ESI) exact mass calculated for C$_{40}$H$_{72}$O$_2$Si$_2$Na (M$^+$+Na) 663.4969. found 663.4971.

(j) Deprotection of hydroxyls in the vitamin D compound 31. (20S)-25-Hydroxy-2-methylene-vitamin D$_3$ (32). To a solution of protected vitamin 31 (8.0 mg) in THF (1 mL) was added tetrabutylammonium fluoride (1.0 M in THF; 595 μL, 595 μmol) at room temperature under argon. The stirring was continued for 20 h, brine was added and the mixture was extracted with ethyl acetate. The organic extracts were dried over MgSO$_4$ and evaporated. The residue was purified by HPLC (9.4 mm×25 cm Zorbax-Sil column, 4 mL/min) using hexane/2-propanol (96:4) solvent system; vitamin 32 (1.18 mg, 23%) was collected at R$_V$ 39 mL. Analytical sample of the vitamin was obtained after HPLC (9.4 mm×25 cm Zorbax Eclipse XDB-C18 column, 4 mL/min) using methanol/water (93:7) solvent system (R$_V$ 35 mL).

32: UV (EtOH) λ$_{max}$ 268.8 nm; $^1$H NMR (200 MHz, CDCl$_3$) δ 0.549 (3H, s, 18-H$_3$), 0.850 (3H, d, J=6.2 Hz, 21-H$_3$), 1.216 (6H, s, 26- and 27-H$_3$), 2.35 (1H, dd, J=13.1, 7.8 Hz, 4β-H), 2.63 (1H, dd, J=13.1, 4.4 Hz, 4α-H), 2.83 (1H, br d, J~13 Hz, 9β-H), 2.89 and 3.14 (1H and 1H, each d, J=14.4 Hz, 1α- and 1β-H), 4.29 (1H, m, 3α-H), 4.84, 4.96 and 5.07 (2H, 1H and 1H, each s, 2×=CH$_2$), 6.08 and 6.32 (1H and 1H, each d, J=11.0 Hz, 7- and 6-H); HRMS (ESI) exact mass calculated for C$_{28}$H$_{44}$O$_2$Na (M$^+$+Na) 435.3239. found 435.3231.

SCHEME I, SCHEME II, SCHEME III and SCHEME IV are set forth below.

SCHEME I

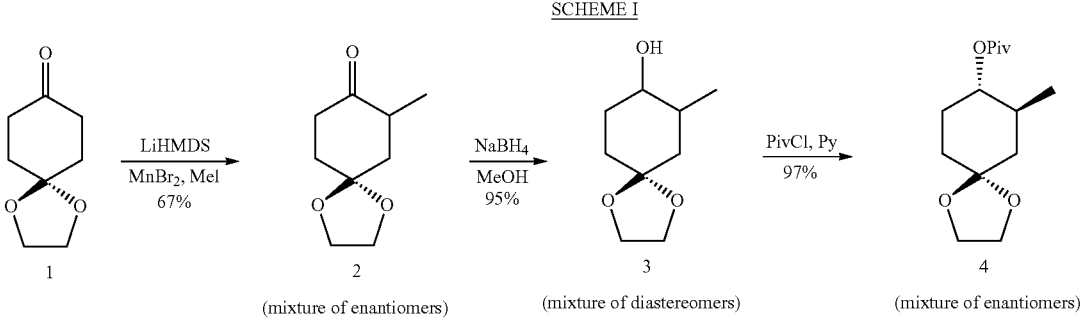

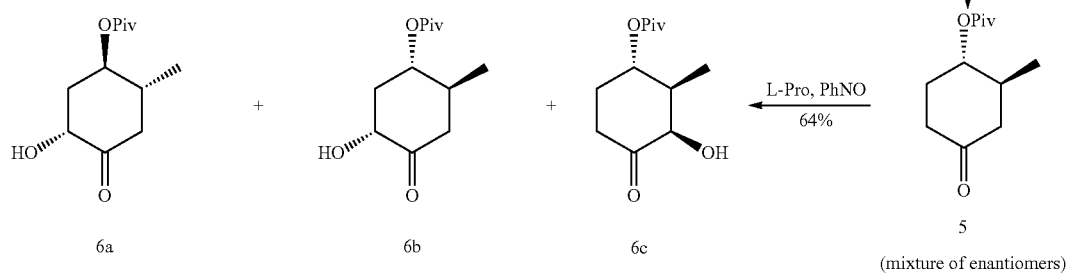

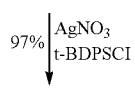

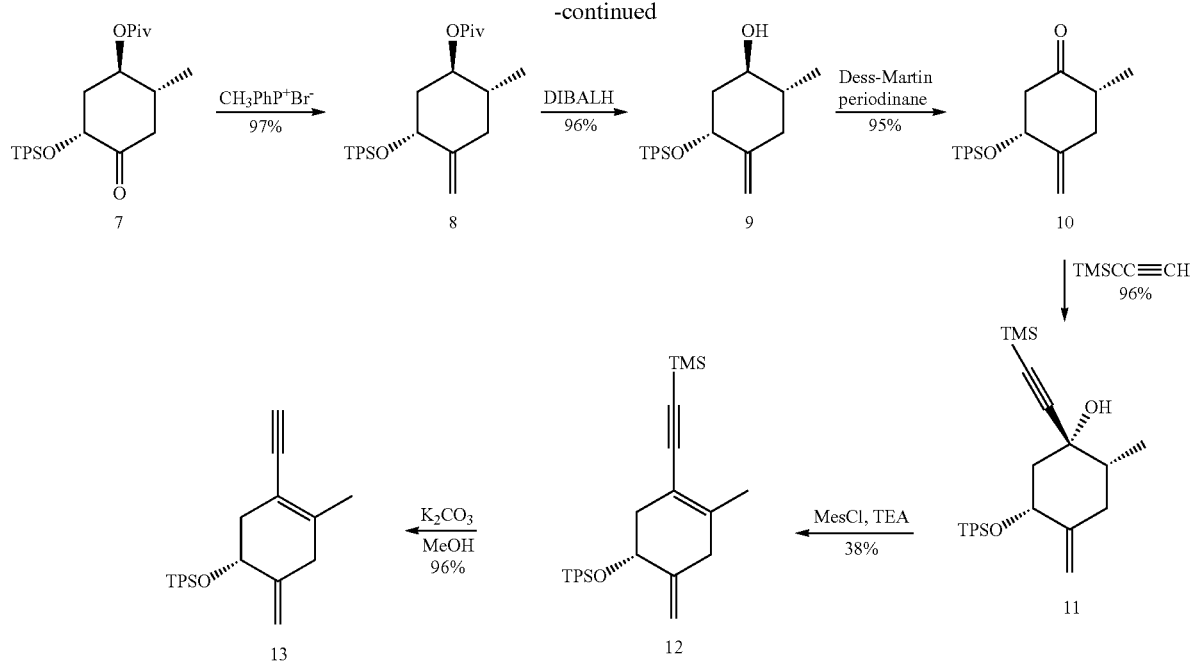
SCHEME II
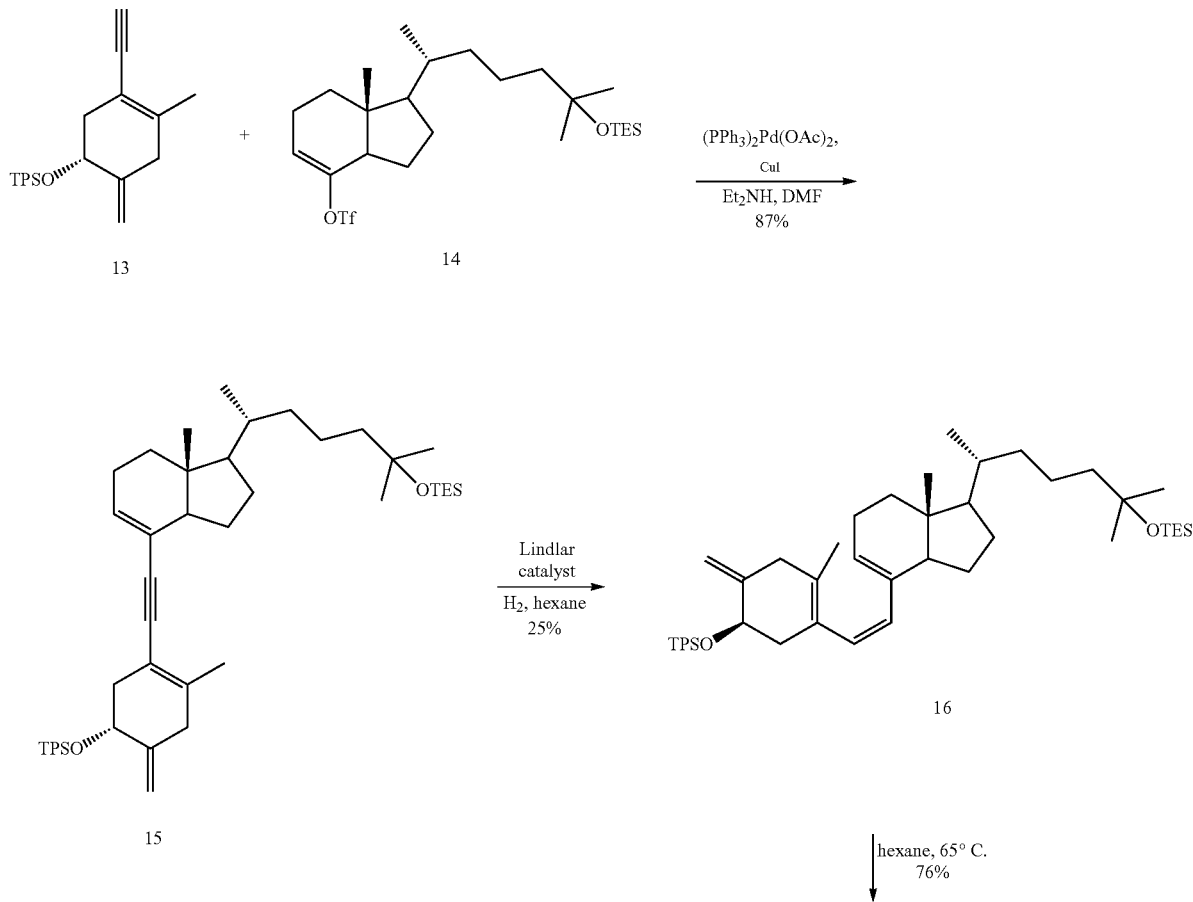

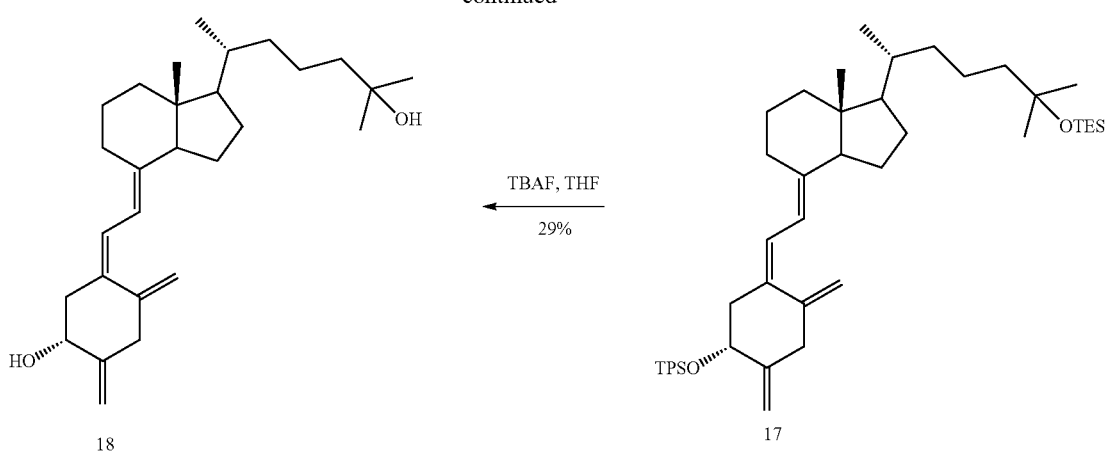
SCHEME III
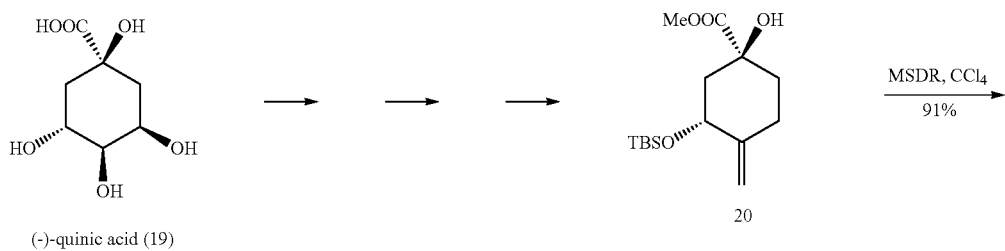
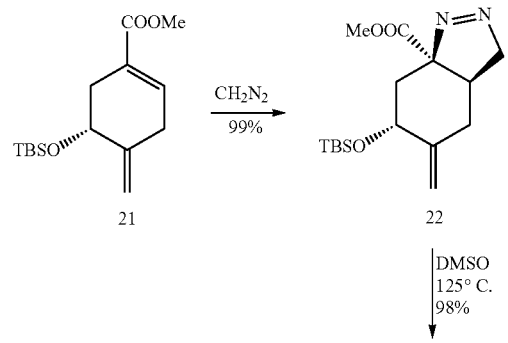
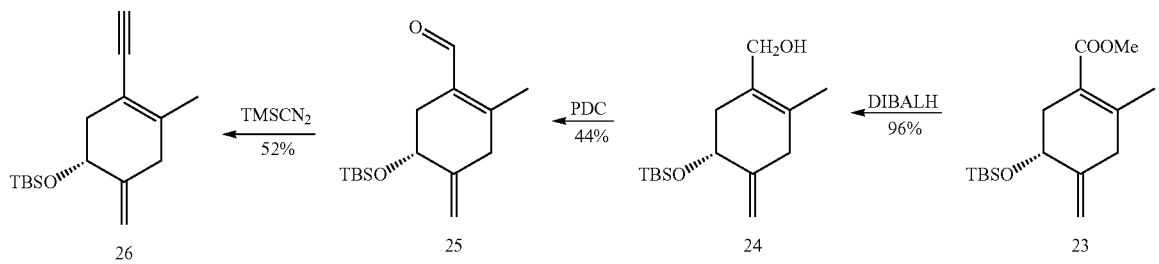

SCHEME IV
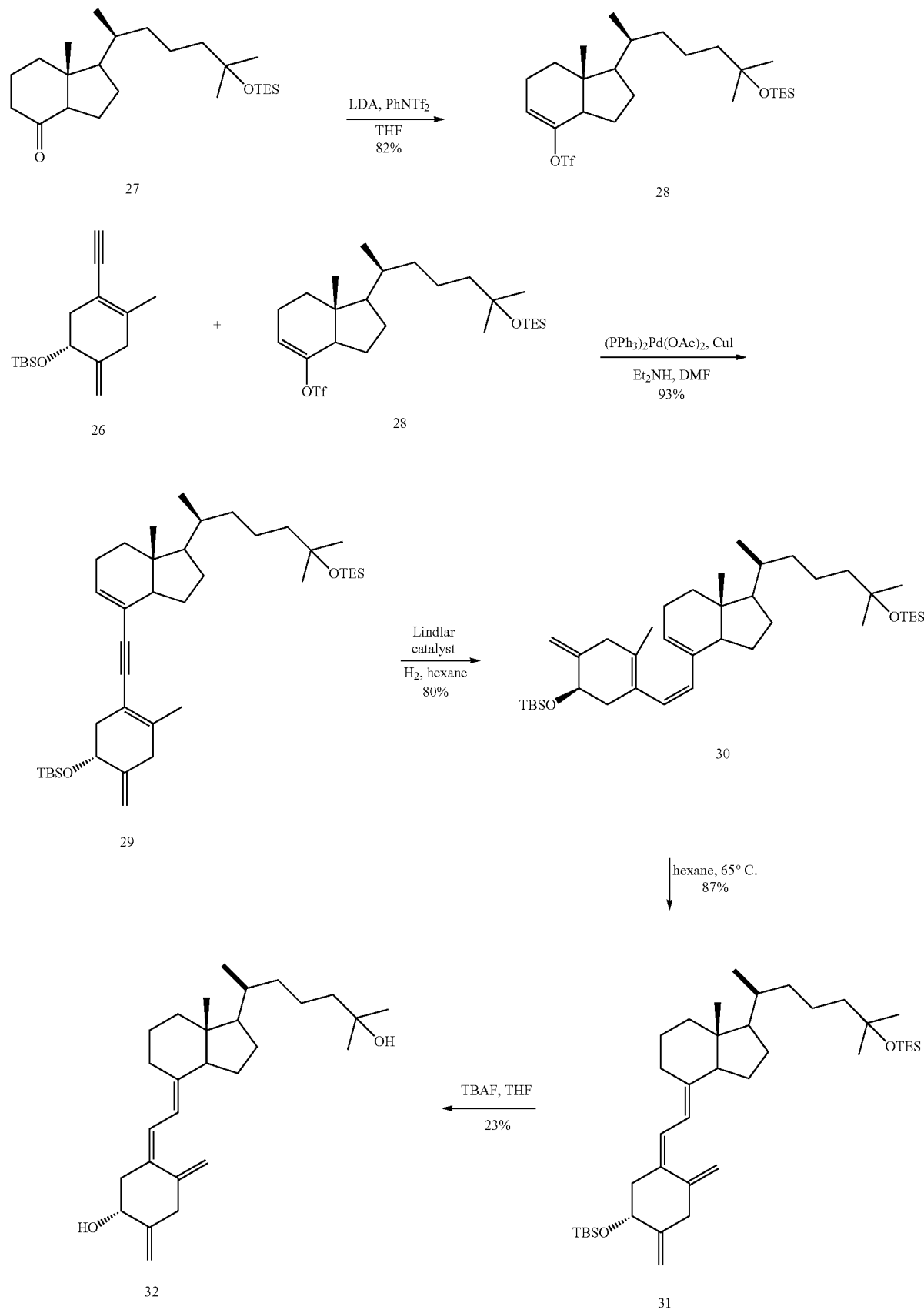

Biological Activity of
(20S)-25-Hydroxy-2-Methylene-Vitamin $D_3$
(1D-QMS)

The introduction of a methylene group to the 2-position, as well as having a methylene substituent at carbon 10, and orienting the methyl group at carbon 20 in its epi or S configuration had little or no effect on binding to the full length recombinant rat vitamin D receptor, as compared to $1\alpha,25$-dihydroxyvitamin $D_3$. The compound 1D-QMS bound with about the same affinity to the receptor as compared to the standard 1,25-$(OH)_2D_3$ (FIG. 1). It might be expected from these results that compound 1D-QMS would have equivalent biological activity. Surprisingly, however, compound 1D-QMS is a highly selective analog with unique biological activity.

Figure 4:
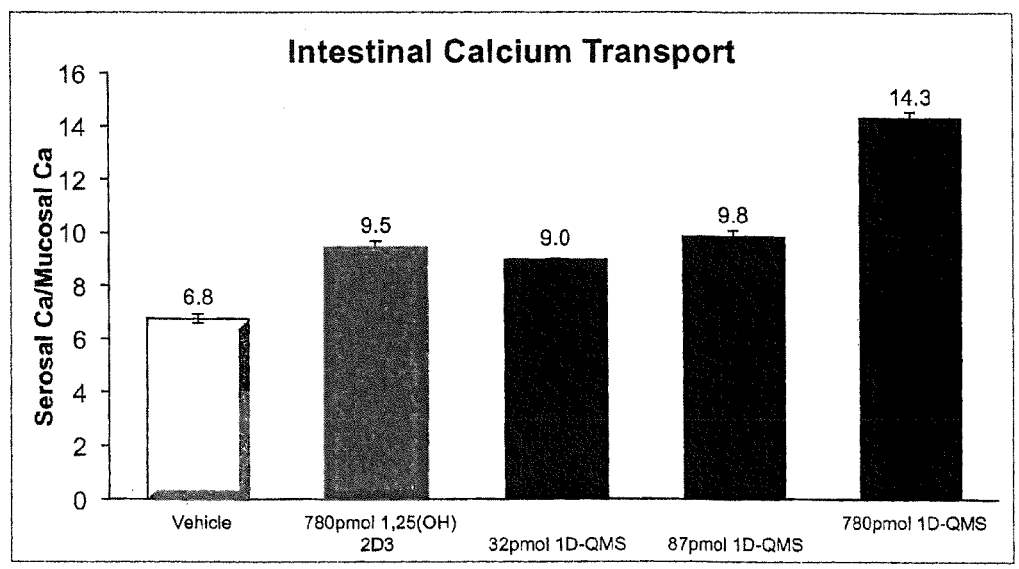

FIG. 4 shows that 1D-QMS has relatively high activity as compared to that of 1,25-dihydroxyvitamin $D_3$ (1,25$(OH)_2D_3$), the natural hormone, in stimulating intestinal calcium transport. 1D-QMS is about equivalent to 1,25$(OH)_2D_3$ in promoting active calcium transport across the gut.

Figure 3:
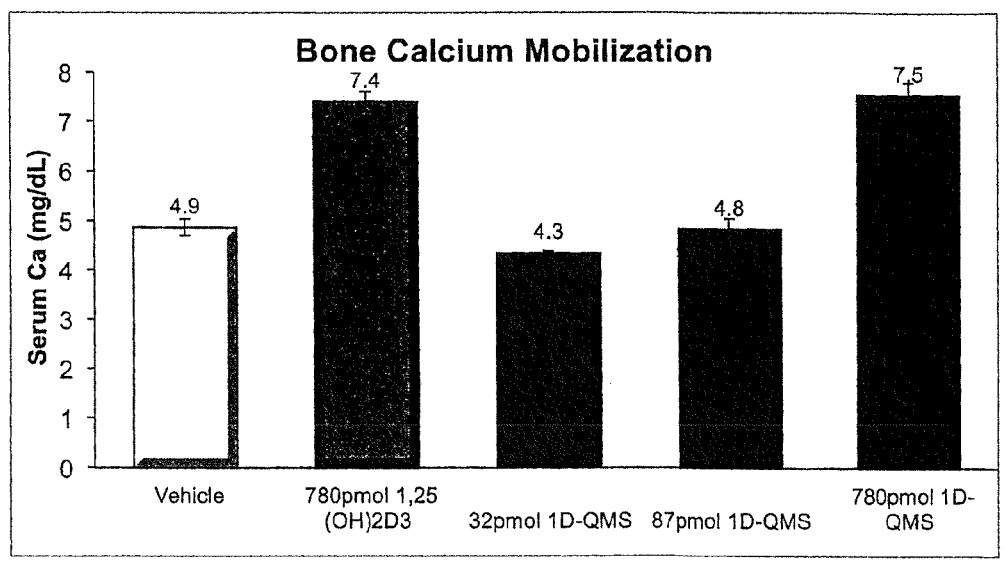

FIG. 3 demonstrates that 1D-QMS has relatively high bone calcium mobilization activity, as compared to 1,25$(OH)_2D_3$. 1D-QMS has about the same potency as the native hormone in releasing bone calcium stores as similar activity is observed when 780 pmol/rat is administered.

FIGS. 3-4 thus illustrate that 1D-QMS may be characterized as having relatively high calcemic activity.

Figure 2:
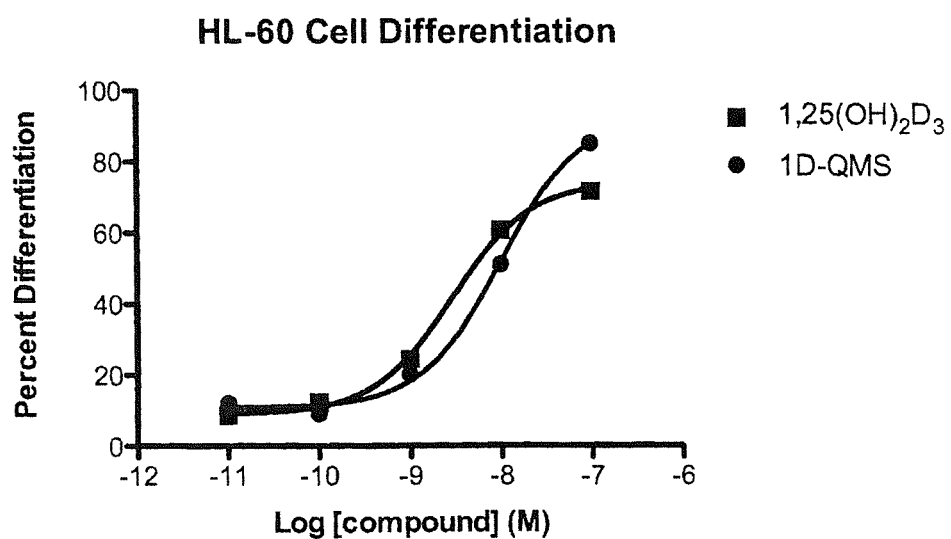

FIG. 2 illustrates that 1D-QMS is almost as potent as 1,25$(OH)_2D_3$ on HL-60 cell differentiation, making it an excellent candidate for the treatment of a cancer, especially for the prevention or treatment of osteosarcoma, leukemia, colon cancer, breast cancer, skin cancer and prostate cancer.

EXPERIMENTAL METHODS

The compounds of the invention were prepared and studied using the following methods.

Vitamin D Receptor Binding

Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at $-80°$ C. until use. For use in binding assays, the protein was diluted in $TEDK_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25$(OH)_2D_3$: molar extinction coefficient=18,200 and $\lambda_{max}$=265 nm). Radiolabeled ligand ($^3H$-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of $\leq 10\%$, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs

The study drugs were dissolved in ethanol and the concentrations determined using UV spectrophotometry. Serial dilutions were prepared so that a range of drug concentrations could be tested without changing the final concentration of ethanol 0.2%) present in the cell cultures.

Cells

Human promyelocytic leukemia (HL60) cells were grown in RPMI-1640 medium containing 10% fetal bovine serum. The cells were incubated at $37°$ C. in the presence of 5% $CO_2$.

Assay Conditions

HL60 cells were plated at $1.2\times10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium
Mobilization

Male, weanling Sprague-Dawley rats were placed on Diet 11 (Suda et al, J. Nutr. 100:1049, 1970) (0.47% Ca)+vitamins AEK for one week followed by Diet 11 (0.02% Ca)+vitamins AEK for 3 weeks. The rats were then switched to the same diet containing 0.47% Ca for one week followed by two weeks on the same diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Interpretation of Data

VDR Binding and HL60 Cell Differentiation.

1D-QMS ($K_i=2\times10^{-10}$M) has about the same activity as the natural hormone 1α,25-dihydroxyvitamin $D_3$ ($K_i=2\times10^{-10}$M) in its ability to compete with [$^3$H]-1,25(OH)$_2$D$_3$ for binding to the full-length recombinant rat vitamin D receptor (FIG. 1). 1D-QMS is also a little less potent ($EC_{50}=1\times10^{-8}$M) in its ability (efficacy or potency) to promote HL60 differentiation as compared to 1α,25-dihydroxyvitamin $D_3$ ($EC_{50}=3\times10^{-9}$M) (See FIG. 2). These data also indicate that 1D-QMS will have significant activity as an anti-cancer agent, especially for preventing or treating osteosarcoma, leukemia, colon cancer, breast cancer, skin cancer and prostate cancer because it has direct cellular activity in causing cell differentiation and in suppressing cell growth.

Calcium Mobilization from Bone and Intestinal Calcium Absorption in Vitamin D-Deficient Animals.

Using vitamin D-deficient rats on a low calcium diet (0.02%), the activities of 1D-QMS and 1,25(OH)$_2$D$_3$ in intestine and bone were tested. As expected, the native hormone (1,25(OH)$_2$D$_3$) increased serum calcium levels at the dosages tested (FIG. 3). FIG. 3 also shows that 1D-QMS has about the same activity in mobilizing calcium from bone as 1,25(OH)$_2$D$_3$. Administration of 1D-QMS at 780 pmol/day for 4 consecutive days resulted in significant mobilization of bone calcium. 1D-QMS is equivalent to the native hormone in releasing bone calcium stores as significant increases in serum calcium are observed at 780 pmol when both 1D-QMS and the native hormone are given.

Intestinal calcium transport was evaluated in the same groups of animals using the everted gut sac method (FIG. 4). These results show that the compound 1D-QMS has about the same ability to promote intestinal calcium transport activity when administered at the recommended lower dosages, as compared to 1,25(OH)$_2$D$_3$. Thus, it may be concluded that 1D-QMS has relatively high intestinal calcium transport activity at the tested doses.

In vivo, distinct activity profiles emerge most likely due to the ability of this compound to act as a prodrug since 1-hydroxylation can occur in a regulated manner and the half-life of the compound is predicted to be extended. This analog may thus serve as an important therapy for diseases where less frequent dose administration is desirable, such as bone diseases like senile osteoporosis, postmenopausal osteoporosis, steroid-induced osteoporosis, low bone turnover osteoporosis, osteomalacia, and renal osteodystrophy.

These results further illustrate that 1D-QMS is an excellent candidate for numerous human therapies as described herein. 1D-QMS is an excellent candidate for treating a cancer because: (1) it has significant VDR binding, transcription activity and cellular differentiation activity; and (2) it is easily synthesized.

Biological Activity of (20R)-25-Hydroxy-2-Methylene-Vitamin $D_3$ (1D-QM)

Figure 5:
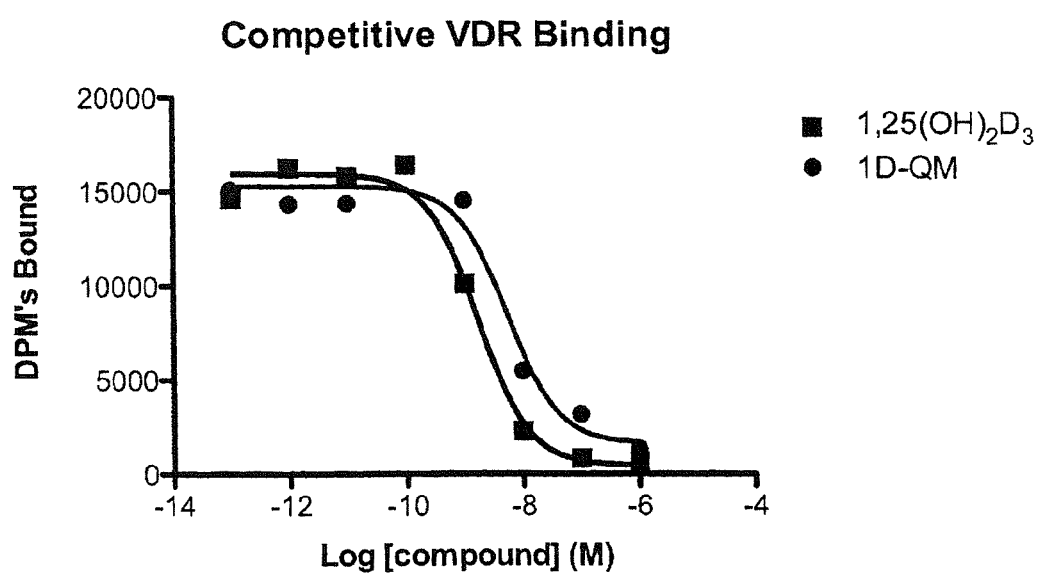
FIGS. 5-8 illustrate various biological activities of (20R)-25-hydroxy-2-methylene-vitamin $D_3$, hereinafter referred to as "1D-QM," as compared to the native hormone 1α,25-dihydroxyvitamin $D_3$, hereinafter "1,25(OH)$_2$D$_3$."

The introduction of a methylene group to the 2-position, as well as having a methylene substituent at carbon 10, and orienting the methyl group at carbon 20 in its natural or R configuration had little or no effect on binding to the full length recombinant rat vitamin D receptor, as compared to 1α,25-dihydroxyvitamin $D_3$. The compound 1D-QM bound with about the same affinity to the receptor as compared to the standard 1,25-(OH)$_2$D$_3$ (FIG. 5). It might be expected from these results that compound 1D-QM would have equivalent biological activity. Surprisingly, however, compound 1D-QM is a highly selective analog with unique biological activity.

Figure 8:
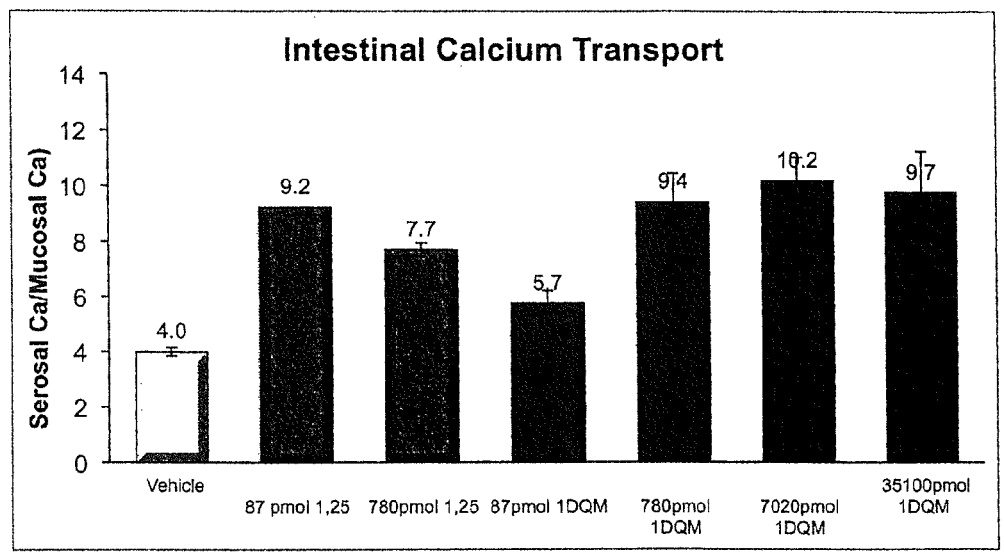

FIG. 8 shows that 1D-QM has relatively high activity as compared to that of 1,25-dihydroxyvitamin $D_3$ (1,25(OH)$_2$D$_3$), the natural hormone, in stimulating intestinal calcium transport. 1D-QM is about equivalent to 1,25(OH)$_2$D$_3$ in promoting active calcium transport across the gut.

Figure 7:
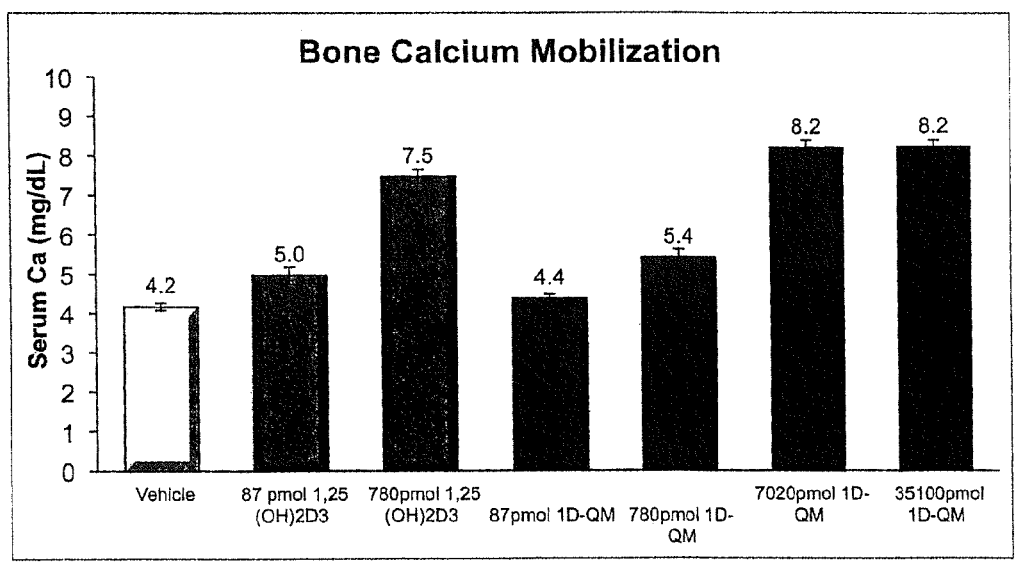

FIG. 7 demonstrates that 1D-QM has relatively low bone calcium mobilization activity, as compared to 1,25(OH)$_2$D$_3$. 1D-QM is less potent than the native hormone in releasing bone calcium stores as little to no activity is observed until 780 pmol/rat is administered; whereas, significant increases in serum calcium are observed at 87 pmol when the native hormone is given.

Figure 6:
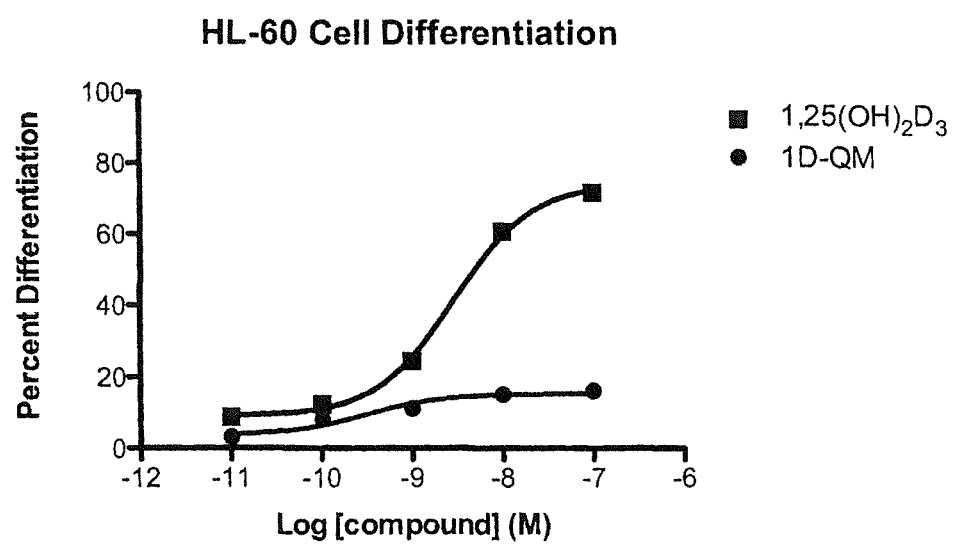

FIG. 6 illustrates that 1D-QM is almost as potent as 1,25 (OH)$_2$D$_3$ on HL-60 cell differentiation, making it an excellent candidate for the treatment of a cancer, especially for the prevention or treatment of osteosarcoma, leukemia, colon cancer, breast cancer, skin cancer and prostate cancer.

Interpretation of Data

VDR Binding and HL60 Cell Differentiation.

1D-QM ($K_i=9\times10^{-10}$M) has about the same activity as the natural hormone 1α,25-dihydroxyvitamin D3 ($K_i=3\times10^{-10}$M) in its ability to compete with [$^3$H]-1,25(OH)$_2$D$_3$ for binding to the full-length recombinant rat vitamin D receptor (FIG. 5). 1D-QM is also a little less potent ($EC_{50}=>10^{-7}$M) in its ability (efficacy or potency) to promote HL60 differentiation as compared to 1α,25-dihydroxyvitamin $D_3$ ($EC_{50}=3\times10^{-9}$M) (See FIG. 6). These data indicate that 1D-QM will have significant activity as an anti-cancer agent, especially for preventing or treating osteosarcoma, leukemia, colon cancer, breast cancer, skin cancer and prostate cancer because it has direct cellular activity in causing cell differentiation and in suppressing cell growth.

Calcium mobilization from bone and intestinal calcium absorption in vitamin D deficient animals. Using vitamin D-deficient rats on a low calcium diet (0.02%), the activities of 1D-QM and 1,25(OH)$_2$D$_3$ in intestine and bone were tested. As expected, the native hormone (1,25(OH)$_2$D$_3$) increased serum calcium levels at the dosages tested (FIG. 7). FIG. 7 also shows that 1D-QM has less activity in mobilizing calcium from bone than 1,25(OH)$_2$D$_3$. Administration of 1D-QM at 87 pmol/day for 4 consecutive days resulted in little or no mobilization of bone calcium. 1D-QM is less potent than the native hormone in releasing bone calcium stores as little to no activity is observed until 780 pmol/rat is administered; whereas, significant increases in serum calcium are observed at 87 pmol when the native hormone is given.

Intestinal calcium transport was evaluated in the same groups of animals using the everted gut sac method (FIG. 8). These results show that the compound 1D-QM is less potent in promoting intestinal calcium transport activity when administered at the recommended lower dosages, as compared to 1,25(OH)$_2$D$_3$.

In vivo, distinct activity profiles emerge most likely due to the ability of this compound to act as a prodrug since 1-hydroxylation can occur in a regulated manner and the half-life of the compound is predicted to be extended. This analog may thus serve as an important therapy for diseases where less frequent dose administration is desirable, such as bone diseases like senile osteoporosis, postmenopausal osteoporosis, steroid-induced osteoporosis, low bone turnover osteoporosis, osteomalacia, and renal osteodystrophy.

These results further illustrate that 1D-QM is an excellent candidate for numerous human therapies as described herein. 1D-QM is an excellent candidate for treating a cancer because: (1) it has significant VDR binding, and cellular differentiation activity; and (2) it is easily synthesized.

For prevention and/or treatment purposes, the compounds of this invention defined by formula I, Ia and Ib may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly 1D-QMS of formula Ia, and 1D-QM of formula Ib, may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly 1D-QMS, and 1D-QM, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly 1D-QMS and 1D-QM, as defined by the above formula I, Ia and Ib as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually or parenterally in dosages of from about 0.01 µg/day to about 1000 µg/day, and preferably from about 0.1 µg/day to about 500 µg/day.

The compounds I, particularly 1D-QMS and 1D-QM, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly 1D-QMS and 1D-QM, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

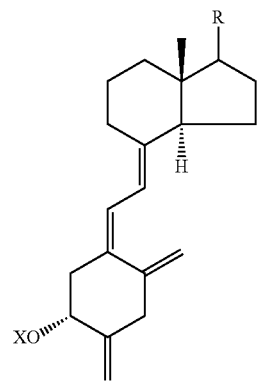

I where X is selected from the group consisting of hydrogen and a hydroxy-protecting group, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

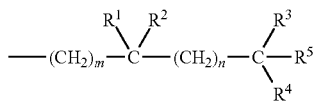

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

2. The compound of claim 1 wherein X is hydrogen.

3. The compound of claim 1 wherein R is selected from:

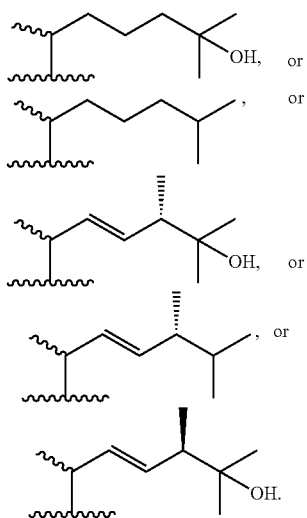

4. The compound of claim 3 wherein X is hydrogen.

5. A pharmaceutical composition containing an effective amount of at least one compound as claimed in claim 1 together with a pharmaceutically acceptable excipient.

6. The pharmaceutical composition of claim 5 wherein said effective amount comprises from about 0.01 μg to about 1000 μg per gram of composition.

7. The pharmaceutical composition of claim 5 wherein said effective amount comprises from about 0.1 μg to about 500 μg per gram of composition.

8. A compound having the formula:

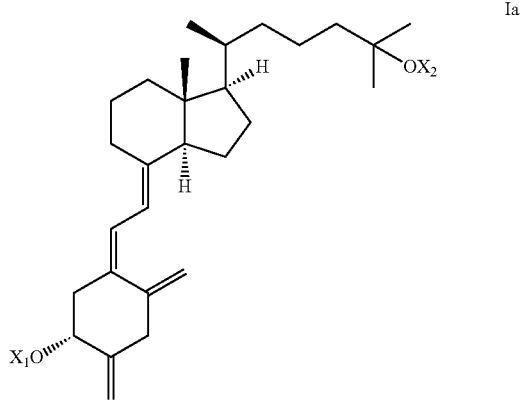

where X$_1$ and X$_2$, which may be the same or different, are each selected from hydrogen or a hydroxy-protecting group.

9. The compound of claim 8 wherein X$_2$ is hydrogen.

10. The compound of claim 8 wherein X$_1$ is hydrogen.

11. The compound of claim 8 wherein X$_1$ and X$_2$ are both t-butyldimethylsilyl.

12. A pharmaceutical composition containing an effective amount of at least one compound as claimed in claim 8 together with a pharmaceutically acceptable excipient.

13. The pharmaceutical composition of claim 12 wherein said effective amount comprises from about 0.01 μg to about 1000 μg per gram of composition.

14. The pharmaceutical composition of claim 12 wherein said effective amount comprise from about 0.1 μg to about 500 μg per gram of composition.

15. A compound having the formula:

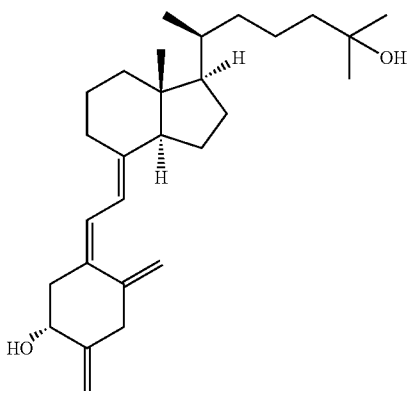 [SMILES: C=C1CC(=C)[C@H](O)C/C1=C/C=C1\CCC[C@]2(C)[C@@H]([C@@H](C)CCCC(C)(C)O)CC[C@@H]12]

and named (20S)-25-hydroxy-2-methylene-vitamin D$_3$.

16. A pharmaceutical composition containing an effective amount of (20S)-25-hydroxy-2-methylene-vitamin D$_3$ together with a pharmaceutically acceptable excipient.

17. The pharmaceutical composition of claim 16 wherein said effective amount comprises from about 0.01 μg to about 1000 μg per gram of composition.

18. The pharmaceutical composition of claim 16 wherein said effective amount comprises from about 0.1 µg to about 500 µg per gram of composition.

19. A compound having the formula:

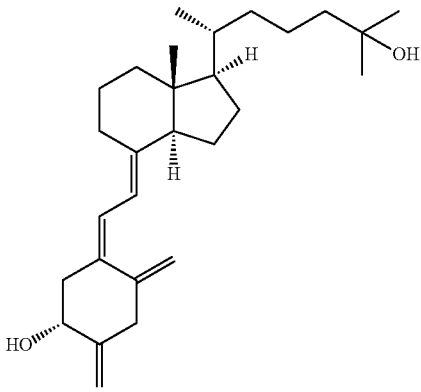 [SMILES: C=C1CC(=C)[C@H](O)C/C1=C/C=C1\CCC[C@]2(C)[C@@H]([C@H](C)CCCC(C)(C)O)CC[C@@H]12]

and named (20R)-25-hydroxy-2-methylene-vitamin $D_3$.

20. A pharmaceutical composition containing an effective amount of (20R)-25-hydroxy-2-methylene-vitamin $D_3$ together with a pharmaceutically acceptable excipient.

21. The pharmaceutical composition of claim 20 wherein said effective amount comprises from about 0.01 µg to about 1000 µg per gram of composition.

22. The pharmaceutical composition of claim 20 wherein said effective amount comprises from about 0.1 µg to about 500 µg per gram of composition.

23. A method of treating a disease selected from the group consisting of osteosarcoma, leukemia, colon cancer, breast cancer, skin cancer or prostate cancer comprising administering to a subject with said disease an effective amount of a 1-desoxy-2-methylene-vitamin D analog having the formula:

I

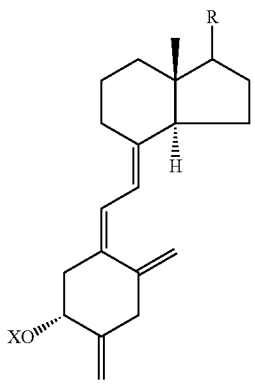

where X is selected from the group consisting of hydrogen and a hydroxy-protecting group, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH=CHY, where the double bond in the side chain may have the cis or trans geometry, and where Y is selected from hydrogen, methyl, —COR$^5$ and a radical of the structure:

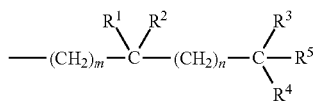

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$—where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

24. The method of claim 23 wherein the vitamin D analog is administered orally.

25. The method of claim 23 wherein the vitamin D analog is administered parenterally.

26. The method of claim 23 wherein the vitamin D analog is administered transdermally.

27. The method of claim 23 wherein the vitamin D analog is administered rectally.

28. The method of claim 23 wherein the vitamin D analog is administered nasally.

29. The method of claim 23 wherein the vitamin D analog is administered sublingually.

30. The method of claim 23 wherein the vitamin D analog is administered in a dosage of from about 0.01 µg/day to about 1000 µg/day.

31. The method of claim 23 wherein the vitamin D analog has the formula:

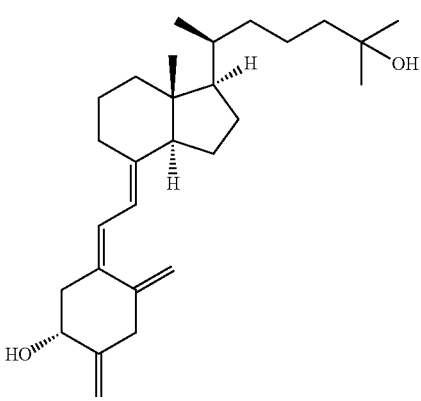 [SMILES: C=C1CC(=C)[C@H](O)C/C1=C/C=C1\CCC[C@]2(C)[C@@H]([C@@H](C)CCCC(C)(C)O)CC[C@@H]12]

and is named (20S)-25-hydroxy-2-methylene-vitamin $D_3$.

32. The method of claim 23 wherein the vitamin D analog has the formula:

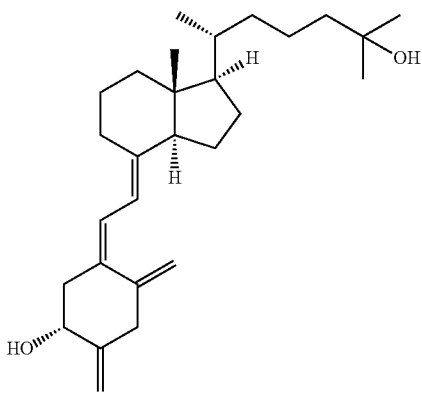 [SMILES: C=C1CC(=C)[C@H](O)C/C1=C/C=C1\CCC[C@]2(C)[C@@H]([C@H](C)CCCC(C)(C)O)CC[C@@H]12]

and is named (20R)-25-hydroxy-2-methylene-vitamin $D_3$.

33. A method of treating metabolic bone disease where it is desired to maintain or increase bone mass comprising administering to a patient with said disease an effective amount of a compound having the formula:

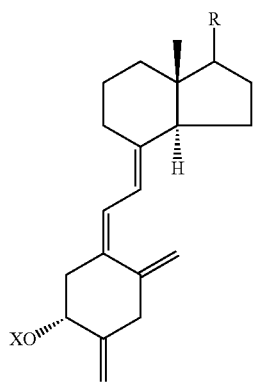

I where X is selected from the group consisting of hydrogen and a hydroxy-protecting group, and where R may be an alkyl, hydrogen, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

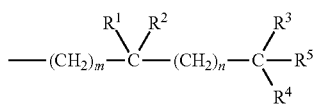

where m and n, independently, represent the integers from 0 to 5, where R$^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula $C_kH_{2k}$— where k is an integer, the group ═CR$^2$R$^3$, or the group —(CH$_2$)$_p$—, where p is an integer from 2 to 5 and where R$^3$ and R$^4$, taken together, represent an oxo group or the group —(CH$_2$)$_q$—, where q is an integer from 2 to 5, and where R$^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

34. The method of claim 33 wherein the compound is administered orally.

35. The method of claim 33 wherein the compound is administered parenterally.

36. The method of claim 33 wherein the compound is administered transdermally.

37. The method of claim 33 wherein the compound is administered rectally.

38. The method of claim 33 wherein the compound is administered nasally.

39. The method of claim 33 wherein the compound is administered sublingually.

40. The method of claim 33 wherein the compound is administered in a dosage of from about 0.01 μg/day to about 1000 μg/day.

41. The method of claim 33 where the disease is senile osteoporosis.

42. The method of claim 33 where the disease is postmenopausal osteoporosis.

43. The method of claim 33 where the disease is steroid-induced osteoporosis.

44. The method of claim 33 where the disease is low bone turnover osteoporosis.

45. The method of claim 33 where the disease is osteomalacia.

46. The method of claim 33 where the disease is renal osteodystrophy.

47. The method of claim 33 wherein the compound has the formula:

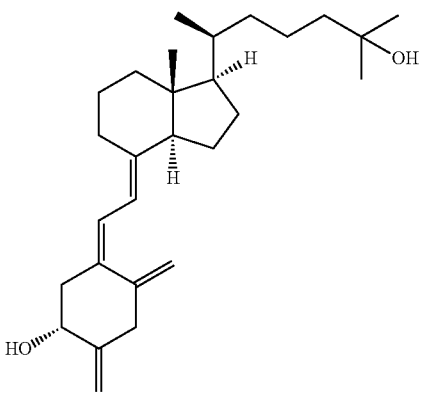 [SMILES: C=C1CC(=C)[C@H](O)C/C1=C/C=C1\CCC[C@]2(C)[C@@H]([C@@H](C)CCCC(C)(C)O)CC[C@@H]12]

and is named (20S)-25-hydroxy-2-methylene-vitamin $D_3$.

48. The method of claim 33 wherein the compound has the formula:
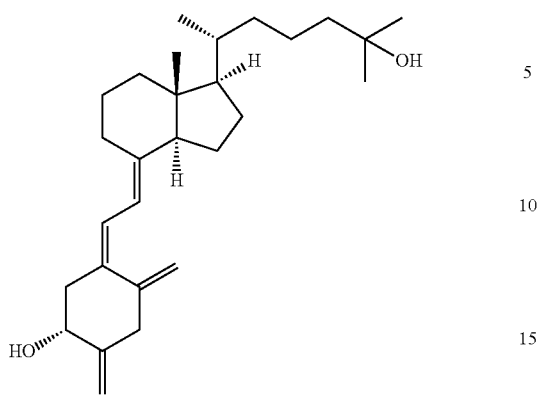
and is named (20R)-25-hydroxy-2-methylene-vitamin $D_3$.
* * * * *